United States Patent
Kimura

(10) Patent No.: US 9,488,711 B2
(45) Date of Patent: Nov. 8, 2016

(54) MAGNETIC RESONANCE IMAGING APPARATUS AND MAGNETIC RESONANCE IMAGING METHOD

(71) Applicant: TOSHIBA MEDICAL SYSTEMS CORPORATION, Otawara-shi, Tochigi (JP)

(72) Inventor: Tokunori Kimura, Yaita Tochigi (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 3 days.

(21) Appl. No.: 14/539,584

(22) Filed: Nov. 12, 2014

(65) Prior Publication Data
US 2015/0131884 A1   May 14, 2015

(30) Foreign Application Priority Data

Nov. 13, 2013   (JP) .................................. 2013-234489

(51) Int. Cl.
| | |
|---|---|
| G06K 9/00 | (2006.01) |
| G01R 33/563 | (2006.01) |
| A61B 5/055 | (2006.01) |
| A61B 5/026 | (2006.01) |
| A61B 5/00 | (2006.01) |
| G01R 33/56 | (2006.01) |
| A61B 5/02 | (2006.01) |

(52) U.S. Cl.
CPC ......... *G01R 33/5635* (2013.01); *A61B 5/0263* (2013.01); *A61B 5/055* (2013.01); *A61B 5/489* (2013.01); *A61B 5/02007* (2013.01); *G01R 33/5602* (2013.01); *G01R 33/5607* (2013.01)

(58) Field of Classification Search
None
See application file for complete search history.

(56) References Cited

U.S. PATENT DOCUMENTS

| | | | | |
|---|---|---|---|---|
| 4,720,679 A * | 1/1988 | Patrick | .................. | G01R 33/24 324/309 |
| 6,564,080 B1 * | 5/2003 | Kimura | ................ | A61B 5/0263 324/307 |
| 8,446,148 B2 * | 5/2013 | Rehwald | ............ | G01R 33/4818 324/309 |
| 2005/0030024 A1 * | 2/2005 | Golay | .................. | G01R 33/561 324/307 |
| 2005/0165296 A1 * | 7/2005 | Ma | ...................... | G01R 33/4828 600/410 |
| 2007/0255129 A1 * | 11/2007 | Du | ...................... | G01R 33/4824 600/410 |
| 2008/0238421 A1 * | 10/2008 | Kitane | ............... | G01R 33/4828 324/307 |
| 2008/0238422 A1 * | 10/2008 | Yui | .................... | G01R 33/4824 324/307 |

(Continued)

OTHER PUBLICATIONS

J. Wang et al., "Simultaneous Noncontrast Angiography and IntraPlaque Hemorrhage (SNAP) Imaging for Carotid Atherosclerotic Disease Evaluation", Magnetic Resonance in Medicine, vol. 69, issue 2, pp. 337-345, Feb. 2013.

(Continued)

*Primary Examiner* — Shervin Nakhjavan
(74) *Attorney, Agent, or Firm* — Nixon & Vanderhye P.C.

(57) ABSTRACT

According to one embodiment, an MRI apparatus includes a data acquiring part and a data processing part. The data acquiring part acquires first and second MR signals by applying at least one IR pulse under an application condition according to a relaxation time of a fluid. The first MR signals include MR signals, having negative values, from the fluid. The second MR signals include MR signals, having positive values, from the fluid. The data processing part generates first and second image data. The first image data depict the fluid as a lower signal region than that of a tissue. The second image data depict the fluid as a higher signal region than that of the tissue. The data processing part generates the first image data with a phase correction based on the second MR signals.

21 Claims, 16 Drawing Sheets

(56) References Cited

U.S. PATENT DOCUMENTS

| | | | | |
|---|---|---|---|---|
| 2010/0045290 A1* | 2/2010 | Miyoshi | ............ | G01R 33/5635 |
| | | | | 324/309 |
| 2011/0018537 A1* | 1/2011 | Warntjes | ............ | G01R 33/5602 |
| | | | | 324/309 |
| 2011/0071382 A1* | 3/2011 | Miyazaki | ............ | A61B 5/0037 |
| | | | | 600/413 |
| 2011/0148413 A1* | 6/2011 | Miyazaki | ............ | G01R 33/482 |
| | | | | 324/309 |
| 2012/0101367 A1* | 4/2012 | Kim | ............ | A61B 5/055 |
| | | | | 600/413 |
| 2012/0262175 A1* | 10/2012 | Alsop | ............ | G01R 33/5607 |
| | | | | 324/314 |
| 2012/0289818 A1* | 11/2012 | van Zijl | ............ | G01R 33/5601 |
| | | | | 600/414 |
| 2013/0194265 A1* | 8/2013 | Rehwald | ............ | G01R 33/4828 |
| | | | | 345/424 |
| 2013/0314086 A1* | 11/2013 | Li | ............ | G01R 33/56509 |
| | | | | 324/309 |

OTHER PUBLICATIONS

J. Wag et al., Improved Carotid Intraplaque Hemorrhage Imaging Using a Slab-Selective Phase-Sensitive Inversion-Recovery (SPI) Sequence, Magnetic Resonance in Medicine, vol. 64, issue 5, pp. 1332-1340, Nov. 2010.

P. Kelleman et al., "Phase-Sensitive Inversion Recovery for detecting Myocardial Infarction Using Gadolinium-Delayed Hyperenhancement", Magnetic Resonance in Medicine, vol. 47, issue 2, pp. 372-383, Feb. 2002.

* cited by examiner (A) $S_{BB}(K_{RO}, K_{PE}, K_{SL})$ (B) $S_{WB}(K_{RO}, K_{PE}, K_{SL})$ (A) |V(BB)|<|V(TISSUE)|

(B) |V(BB)|>|V(TISSUE)|

MAGNETIC RESONANCE IMAGING APPARATUS AND MAGNETIC RESONANCE IMAGING METHOD

CROSS REFERENCES TO RELATED APPLICATIONS

This application is based upon and claims the benefit of priority from Japanese Patent Application No. 2013-234489, filed on Nov. 13, 2013; the entire contents of which are incorporated herein by reference.

Further, the entire contents of Japanese Patent Application No. 2014-164335, filed on Aug. 12, 2014 are incorporated herein by reference.

FIELD

Embodiments described herein relate generally to an MRI (magnetic resonance imaging) apparatus and a magnetic resonance imaging method.

BACKGROUND

The MRI apparatus is an imaging diagnostic apparatus which magnetically excites nuclear spins of an object set in a static magnetic field with RF (radio frequency) signals having the Larmor frequency and reconstructs an image based on MR (magnetic resonance) signals generated due to the excitation.

As one of image generating methods in an MRI apparatus, real part imaging is known. The real part imaging is an image generating method for performing imaging processing using not absolute values but real parts of complex signals to be an imaging target. In real part imaging, a technique for selectively acquiring MR signals from blood as negative signals by applying a single or multiple IR (inversion recovery) pulses is devised.

According to this method, intensities of MR signals from blood which flows inside blood vessels can be suppressed. For this reason, real part imaging of blood with application of an IR pulse or IR pulses makes it possible to depict the blood as low signal regions with an improved CNR (contrast to noise ratio). In this case, the background tissues are depicted whitely as high signal regions while blood is depicted blackly.

Such a blood flow image on which blood is depicted blackly is called BB (black blood) image. The BB image can be acquired as a longitudinal relaxation (T1) weighted image (T1W), a transverse relaxation (T2) weighted image (T2W), or a proton density weighted image (PDW).

When a BB image is acquired as a T1W, an IR pulse is applied as a prepulse to a slab larger than an imaging slab to be imaged before MR data for imaging are acquired. Thereby, the longitudinal magnetizations Mz of static tissues and blood in an application region of the IR pulse are inverted. Then, a TI (inversion time) is set so that imaging data are acquired at timing before timing at which the longitudinal magnetization Mz of the blood becomes zero due to the longitudinal relaxation (T1 relaxation). Note that, the TI is a time from an application timing of an IR pulse to that of an RF excitation pulse for acquiring imaging data.

Moreover, an application region of an IR pulse is set to be a region, which is larger than an imaging slab, considering a flow velocity of blood and the T1 relaxation of the blood so that blood flowing from the outside of the imaging slab into the imaging slab becomes a target of the IR pulse application at an acquisition timing of imaging data. That is, blood which flows into an imaging slab at an acquisition timing of imaging data is also an inversion target of the longitudinal magnetization Mz by the application of an IR pulse.

When a readout of MR signals is performed by a gradient echo (GRE) type of sequence, such as a fast field echo (FFE) sequence, under such conditions, MR signals from the background tissues become positive values while MR signals from the blood become zero or negative values. Therefore, a T1W can be generated as a BB image in which the blood is depicted blackly.

On the other hand, in the case that a BB image is acquired as a T2W or a PDW, data acquisition conditions with application of multiple IR pulses, consisting of region selective IR pulses and non-region selective IR pulses, are set. Specifically, the application conditions of multiple IR pulses, including the number of pulses, application timings, and application regions of the IR pulses, are determined so that the longitudinal magnetization Mz of the static background tissues does not invert while only the longitudinal magnetization Mz of the blood flowing into an imaging slab inverts.

When a readout of MR signals is performed with a TI, with which imaging data are acquired at timing before the timing when the longitudinal magnetization Mz of the blood becomes zero due to the T1 relaxation, under such application conditions of IR pulses, the MR signals from the blood have zero or negative values. Therefore, a T2W or a PDW can be generated as a BB image in which the blood is depicted blackly.

Furthermore, in addition to acquisition of a BB image by the real part imaging accompanied by application of IR pulses, the method for generating a WB (white blood) image in which blood is depicted whitely as a high signal region has also been proposed. Specifically, the technique, which generates a WB image by inversion and maximum intensity projection (MIP) processing of brightness of a BB image, has been proposed.

In an MRA (magnetic resonance angiography) for imaging blood and blood vessels, it is desired to acquire both a BB image and a WB image with improved CNRs. However, it is difficult to obtain sufficient CNRs by the conventional method for generating a WB image using a BB image as original data. Accordingly, imaging for acquiring a WB image is separately performed by a TOF (time of flight) method or the like, in many cases.

Moreover, generating a BB image by real part imaging requires a phase correction of MR signals from background tissues. The phase correction requires image data in which not only MR signals from background tissues but MR signals from blood show positive values. For this reason, it is necessary to acquire each image for the phase correction with TI set to a long interval so that the longitudinal magnetization Mz of the blood becomes a positive value. That is, imaging for acquiring images for a phase correction is separately required in order to generate a BB image by real part imaging.

Accordingly, an object of the present invention is to provide a magnetic resonance imaging apparatus and a magnetic resonance imaging method which can acquire a necessary image, such as a BB image and a WB image, having an improved CNR with fewer number of times of imaging or less imaging time to increase efficiency of the MRI apparatus and method.

DETAILED DESCRIPTION

Figure 1:
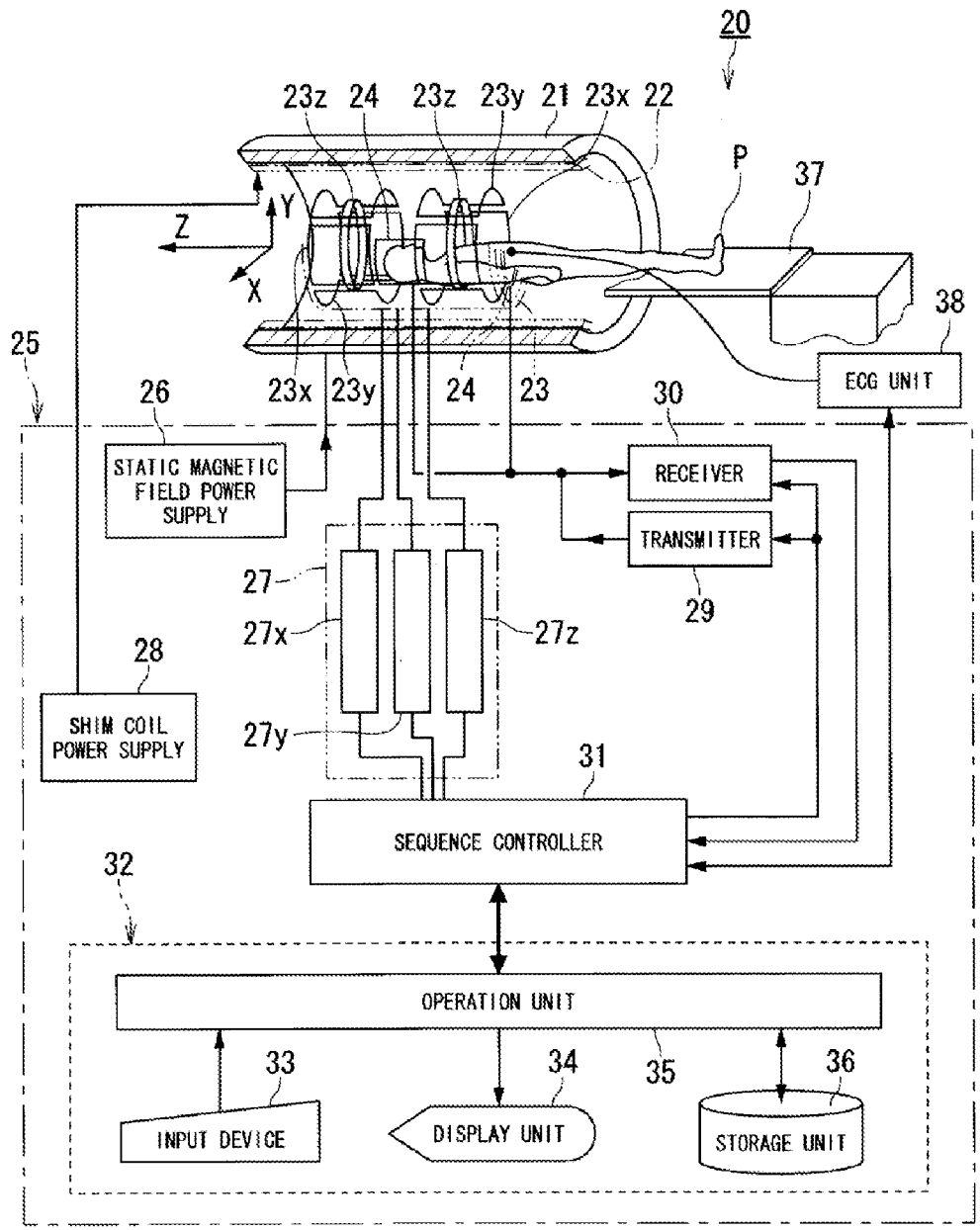
FIG. 1 is a block diagram showing a magnetic resonance imaging apparatus according to the first embodiment of the present invention.

In general, according to one embodiment, a magnetic resonance imaging apparatus includes a data acquiring part and a data processing part. The data acquiring part is configured to acquire first magnetic resonance signals and second magnetic resonance signals from a same imaging area of an object by applying at least one inversion recovery pulse under an application condition according to a relaxation time of a fluid. The first magnetic resonance signals include magnetic resonance signals, having negative values, from the fluid. The second magnetic resonance signals include magnetic resonance signals, having positive values, from the fluid. The data processing part is configured to generate first image data and second image data based on the first magnetic resonance signals and the second magnetic resonance signals. The first image data depict the fluid as a lower signal region than a signal region of a tissue. The second image data depict the fluid as a higher signal region than a signal region of the tissue. The data processing part is configured to generate the first image data with a phase correction based on the second magnetic resonance signals.

Further, according to another embodiment, a magnetic resonance imaging apparatus includes a data acquiring part and a data processing part. The data acquiring part is configured to acquire magnetic resonance signals from an imaging area of an object by applying at least one inversion recovery pulse under an application condition according to relaxation times of a first component to be a suppression target and a second component to be a weighted target. The magnetic resonance signals include signals, having negative values, from the first component and signals, having positive values, from the second component. The magnetic resonance signals correspond to an asymmetric sampling region in at least one direction in a k-space. The data processing part is configured to generate image data by data processing including a phase correction of real space signals generated based on the magnetic resonance signals and processing for imaging real parts of the real space signals after the phase correction. The image data depict the first component as a lower signal region than a signal region of the second component.

Further, according to another embodiment, a magnetic resonance imaging method includes acquiring first magnetic resonance signals and second magnetic resonance signals from a same imaging area of an object by applying at least one inversion recovery pulse under an application condition according to a relaxation time of a fluid; and generating first image data and second image data based on the first magnetic resonance signals and the second magnetic resonance signals. The first magnetic resonance signals include magnetic resonance signals, having negative values, from the fluid. The second magnetic resonance signals include magnetic resonance signals, having positive values, from the fluid. The first image data depict the fluid as a lower signal region than a signal region of a tissue. The second image data depict the fluid as a higher signal region than a signal region of the tissue. The first image data are generated with a phase correction based on the second magnetic resonance signals.

A magnetic resonance imaging apparatus and a magnetic resonance imaging method according to embodiments of the present invention will be described with reference to the accompanying drawings.

First Embodiment

FIG. 1 is a block diagram showing a magnetic resonance imaging apparatus according to the first embodiment of the present invention.

A magnetic resonance imaging apparatus 20 includes a cylinder-shaped static field magnet 21, a shim coil 22, a gradient coil 23 and RF coils 24. The static field magnet 21 generates a static magnetic field. The shim coil 22 is arranged inside the static field magnet 21.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z, which is cylinder-shaped, is arranged inside the static field magnet 21. The gradient coil 23 has also a bed 37 in the area formed inside it which is an imaging area. The bed 37 supports an object P. The RF coils 24 include a WBC (whole body coil), which is built in a gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Gz in the X, Y and Z directions in the imaging area.

The RF coils 24 communicate with the transmitter 29 and/or the receiver 30. The transmission RF coil 24 transmits RF signals given from the transmitter 29 to the object P. The reception RF coil 24 receives MR signals generated due to nuclear spins inside the object P which are excited by the RF signals to give to the receiver 30.

The sequence controller 31 of the control system 25 communicates with the gradient power supply 27, the transmitter 29 and the receiver 30. The sequence controller 31 stores sequence information describing control information needed in order to drive the gradient power supply 27, the transmitter 29 and the receiver 30, and generates gradient magnetic fields Gx, Gy and Gz in the X, Y and Z directions and RF signals by driving the gradient power supply 27, the transmitter 29 and the receiver 30 according to a predetermined stored sequence. The above-described control information includes motion control information, such as intensities, application durations and application timings of electric current pulses which should be applied to the gradient power supply 27.

The sequence controller 31 is also configured to give raw data to the computer 32. The raw data, which are complex-valued data, are generated by the receiver 30 performing detection and A/D (analog to digital) conversion of MR signals.

The transmitter 29 gives RF signals to the RF coil 24 in accordance with control information provided from the sequence controller 31. Meanwhile, the receiver 30 performs detection, necessary signal processing and A/D conversion of MR signals given from the RF coils 24 to generate raw data which are digitized complex-valued data. The generated raw data are given from the receiver 30 to the sequence controller 31.

In addition, an ECG (electro cardiogram) unit 38 for acquiring an ECG signal of the object P is provided to the magnetic resonance imaging apparatus 20. The ECG signal detected by the ECG unit 38 is output to the computer 32 through the sequence controller 31.

The computer 32 has various functions by the operation unit 35 executing programs stored in the storage unit 36 of the computer 32. Alternatively, specific circuits having various functions may be provided with the magnetic resonance imaging apparatus 20, instead of at least a part of the computer programs.

Figure 2:
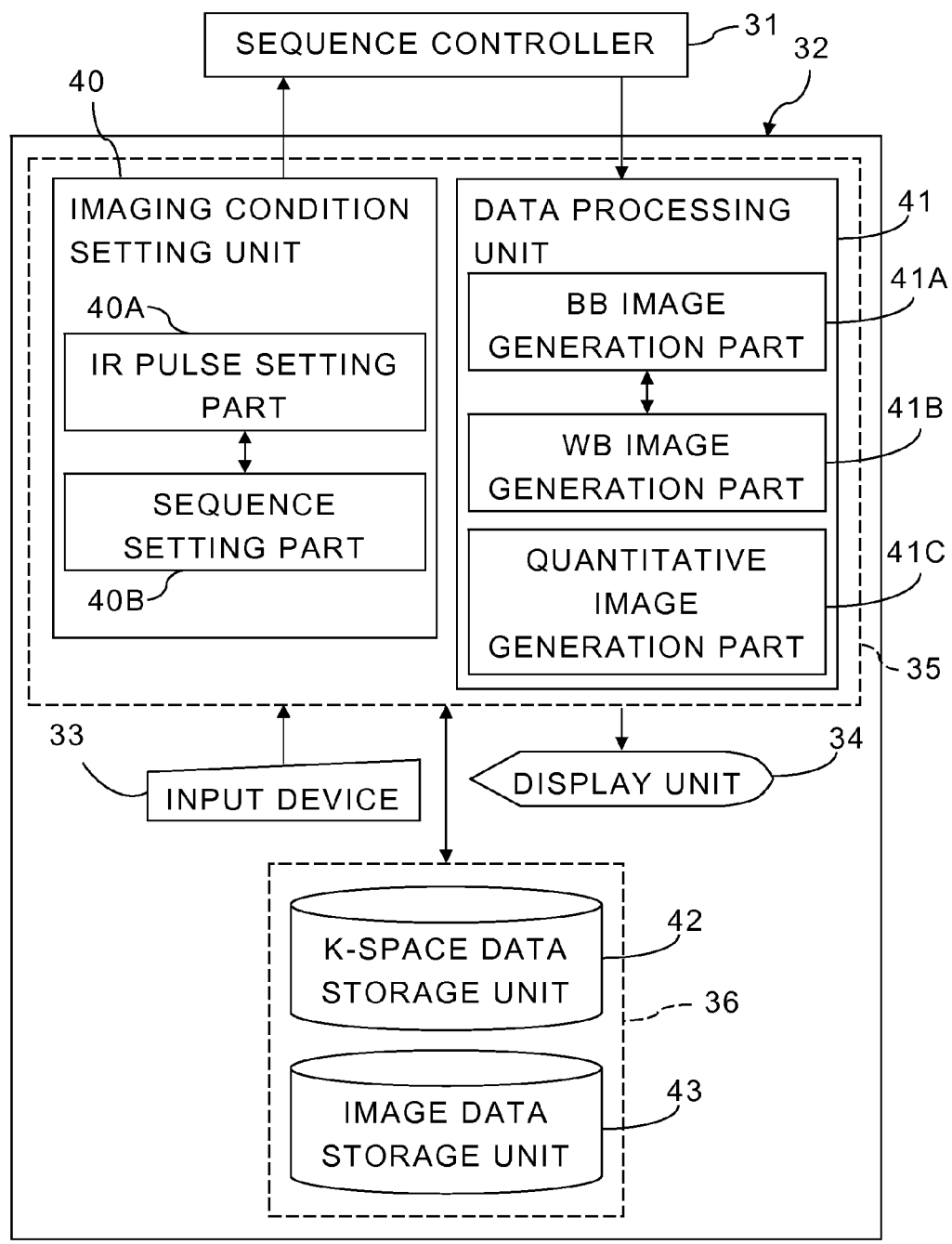
FIG. 2 is a functional block diagram of the computer shown in FIG. 1.

FIG. 2 is a functional block diagram of the computer 32 shown in FIG. 1.

The operation unit 35 of the computer 32 functions as an imaging condition setting unit 40 and a data processing unit 41 by executing program stored in the storage unit 36. The imaging condition setting unit 40 has an IR pulse setting part 40A and a sequence setting part 40B. The data processing unit 41 has a BB image generation part 41A, a WB image generation part 41B, and a quantitative image generation part 41C. Moreover, the storage unit 36 functions as a k-space data storage unit 42 and an image data storage unit 43.

The imaging condition setting unit 40 has a function to set imaging conditions including a pulse sequence based on direction information from the input device 33 and output the set imaging conditions to the sequence controller 31. Especially, the imaging condition setting unit 40 has a function to set imaging conditions to obtain both BB image data and WB image data, in an imaging area, as blood flow image data, blood vessel image data or blood vessel wall image (VWI: Vessel Wall Image) data by an IR method and imaging processing including real part imaging.

BB image data is image data in which blood is depicted, as lower signals regions, more blackly than tissues. Moreover, WB image data is image data in which blood is depicted, as high signal regions, more whitely than tissues.

The IR method is an imaging method which inverts longitudinal magnetization by application of a single or multiple IR pulses and acquires imaging data, which are MR signals for generating image data, after a TI. Note that, IR pulses include region selective IR pulses, whose application regions can be set, and non-region selective IR pulses, whose application regions cannot be set.

Meanwhile, the real part imaging is an image generating method which generates target diagnostic image data by imaging processing using real parts of image signals which are complex signals generated as intermediate data in image reconstruction processing. The real part imaging is applied to a generation of BB image data. On the other hand, WB image data are generated by conventional imaging processing, which is not the real part imaging, i.e., imaging processing which generates image data using absolute values of image signals which are complex signals.

Thus, the imaging condition setting unit 40 has a function to set imaging conditions for acquiring BB image data as the first image data and WB image data as the second image data by data acquisitions with applying IR pulses and real part imaging.

The data acquisition conditions for acquiring both BB image data and WB image data by an IR method and real part imaging are to be conditions for acquiring the first MR signals for generating BB image data, which are the first image data, with IR pulse application, and also for acquiring the second MR signals for generating WB image data, which are the second image data, from a same imaging area.

The first MR signals for generating BB image data are to be a target of real part imaging for depicting a blood-occupying region as a low signal region. On the other hand, the second MR signals for generating WB image data are desired to be acquired, so that absolute values of MR signals from blood have as large values as possible, in order to depict blood-occupying regions with high signal values. For that purpose, it is necessary to acquire the first MR signals so that MR signals from blood have negative values and to acquire the second MR signals so that MR signals from the blood have positive values.

For these reasons, in the imaging condition setting unit 40, data acquisition conditions for acquiring the first MR signals, for generating BB image data, of which MR signals from blood have negative values, and for acquiring the second MR signals, for generating WB image data, of which MR signals from the blood have positive values, by applying an IR pulse or IR pulses under application conditions according to at least the relaxation time of the blood, are set.

The IR pulse setting part 40A of the imaging condition setting unit 40 has a function to set application conditions of IR pulses, such as the number of pulses, application regions, and TIs, so as to acquire the first MR signals, of which MR signals from blood have negative values, and the second MR signals, of which MR signals from the blood have positive values. Examples of the above mentioned application conditions of an IR pulse or IR pulses include a condition to respectively acquire the first MR signals, of which at least MR signal components from blood flowing into an imaged part of tissues have been influenced by at least one IR pulse, and the second MR signals, of which MR signal components from blood flowing into the imaged part of tissues have not been influenced by IR pulses. That is, application conditions of an IR pulse or IR pulses have only to be set so as to be able to acquire both the first MR signals, of which MR signal components from blood have negative values, and the second MR signals, of which MR signal components from blood have positive values.

Note that, MR signal components from an imaged part of tissues may be or may not be influenced by an IR pulse or IR pulses, in both the first MR signals and the second MR signals. However, it is a condition for obtaining a preferable contrast to acquire the first MR signals, of which MR signals from tissues have positive values and MR signals from blood have negative values, for generating BB image data.

On the other hand, the sequence setting part 40B has a function to set a pulse sequence for acquiring each of the first MR signals and the second MR signals as imaging data. Application conditions of IR pulses and a pulse sequence are determined so that the application conditions of IR pulses correspond to the pulse sequence. That is, a pulse sequence according to application conditions of IR pulses is set. On the contrary, IR pulse application conditions according to a pulse sequence are set.

The first MR signals and the second MR signals can be acquired with TIs which can be considered to be the same. On the contrary, the first MR signals and the second MR signals may also be acquired with mutually different TIs. In the case that the first MR signals and the second MR signals are acquired with TIs which are considered to be the same, it is necessary to set the first IR pulse for acquiring the first MR signals and the second IR pulse for acquiring the second MR signals as application conditions of IR pulses. On the other hand, in the case that the first MR signals and the second MR signals are acquired with different TIs, data acquisition conditions for acquiring the first MR signals and the second MR signals after applying a common IR pulse may be set. Alternatively, the first IR pulse for acquiring the first MR signals and the second IR pulse for acquiring the second MR signals may be set individually. Otherwise, the second MR signals, of which MR signals from blood have positive values, may be acquired without applying an IR pulse at first, and subsequently, an IR pulse may be applied to acquire the first MR signals, of which MR signals from tissues have positive values and MR signals from the blood have negative values.

When the first MR signals and the second MR signals are acquired with TIs which can be considered to be the same, intensities of MR signals from tissues, included in the first MR signals, can be equivalent to intensities of MR signals from the tissues, included in the second MR signals. Therefore, WB image data having an improved CNR can be generated, as image data in which blood is depicted with suppressed tissue depiction, by data processing including subtraction processing between image data generated based on the first MR signals and image data generated based on the second MR signals.

Accordingly, a concrete example of data acquisition conditions for acquiring the first MR signals and the second MR signals with TIs which can be considered to be the same will be explained firstly. In this case, application conditions of the first IR pulse, by which the longitudinal magnetization Mz of blood becomes a negative value due to the T1 relaxation during a TI after the IR pulse application, and application conditions of the second IR pulse, by which the longitudinal magnetization Mz of the blood becomes a positive value due to the T1 relaxation during a TI after the IR pulse application, are set in the IR pulse setting part 40A. Furthermore, pulse sequences corresponding to the TI are set in the sequence setting part 40B.

At first, the first example for applying the first IR pulse for generating BB image data to an area larger than an imaging area and the second IR pulse for generating WB image data to a narrow area covering the imaging area in order to acquire each of the BB image data and the WB image data as T1W data will be explained.

Figure 3:
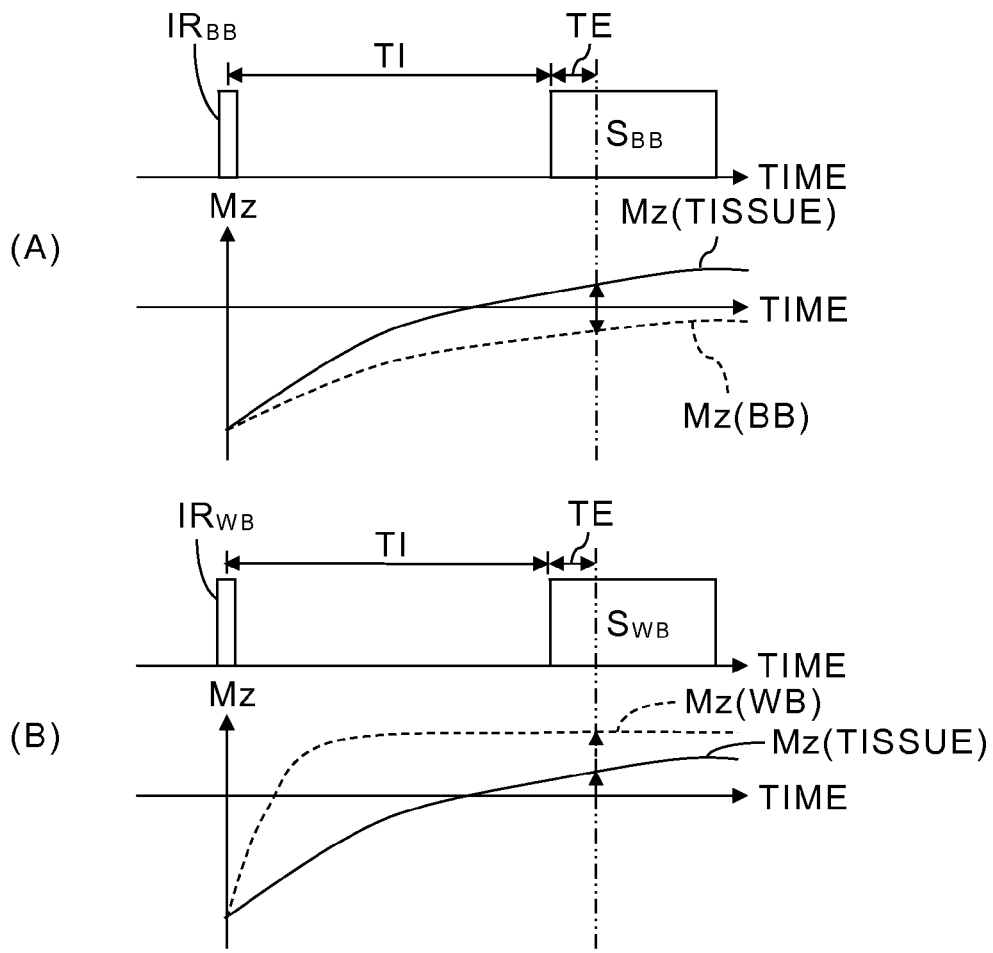
FIG. 3 is a chart showing an application timing of a single IR pulse for acquiring each of BB image data and WB image data as T1W data.
Figure 4:
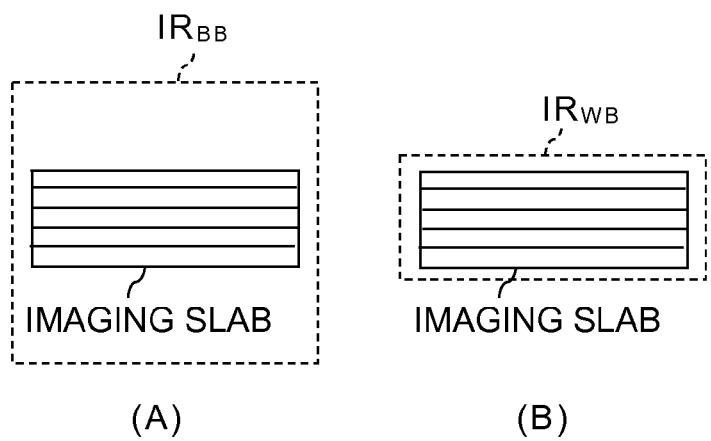
FIG. 4 is a view showing application areas of the first IR pulse and the second IR pulse shown in FIG. 3.

FIG. 3 is a chart showing an application timing of a single IR pulse for acquiring each of BB image data and WB image data as T1W data. FIG. 4 is a view showing application areas of the first IR pulse and the second IR pulse shown in FIG. 3.

In (A) and (B) of FIG. 3, each horizontal axis represents time while the vertical axis of each graph represents longitudinal magnetizations Mz of blood and tissues. In FIG. 3, (A) shows application timing of the first IR pulse $IR_{BB}$ for acquiring the first MR signals $S_{BB}$ for the BB image data and time changes of the longitudinal magnetization Mz (TISSUE) of the tissues and the longitudinal magnetization Mz (BB) of the blood after applying the first IR pulse $IR_{BB}$. Meanwhile, (B) in FIG. 3 shows application timing of the second IR pulse $IR_{WB}$ for acquiring the second MR signals $S_{WB}$ for the WB image data and time changes of the longitudinal magnetization Mz (TISSUE) of the tissues and the longitudinal magnetization Mz (BB) of the blood after applying the second IR pulse $IR_{WB}$.

As shown in FIG. 3 (A), the first data acquisition conditions for performing a data acquisition sequence which acquires the first MR signals $S_{BB}$ with a TI and an appropriate TE (echo time) after applying the first IR pulse $IR_{BB}$ for the BB image data can be set. Similarly, as shown in FIG. 3 (B), the second data acquisition conditions for performing a data acquisition sequence which acquires the second MR signals $S_{WB}$ with the TI and the appropriate TE after applying the second IR pulse $IR_{WB}$ for the WB image data can be set.

Furthermore, as shown in FIG. 4 (A), an application region of the first IR pulse $IR_{BB}$ for the BB image data can be set as a region enough larger than an imaging slab which is an acquisition target of the first MR signals $S_{BB}$. Meanwhile, as shown in FIG. 4 (B), an application region of the second IR pulse $IR_{WB}$ for the WB image data can be set as a region which covers the imaging slab and is narrower than the application region of the first IR pulse $IR_{BB}$.

Then, as shown in FIG. 3 (A), the polarities of the longitudinal magnetization Mz(TISSUE) of the tissues and the longitudinal magnetization Mz(BB) of the blood in the application region of the first IR pulse $IR_{BB}$ invert and become negative values at the application timing of the first IR pulse $IR_{BB}$. Subsequently, the longitudinal magnetization Mz(TISSUE) of the tissues changes to a positive value gradually with the lapse of time according to the T1 of the tissues as a time constant because of the T1 relaxation. Similarly, the longitudinal magnetization Mz(BB) of the blood also changes to a positive value gradually with the lapse of time according to the T1 of the blood as a time constant because of the T1 relaxation.

However, the T1 of the blood is longer than the T1 of the tissues, such as a muscle and a plaque. Therefore, the longitudinal magnetization Mz(BB) of the blood is still a negative value at the timing when the longitudinal magnetization Mz(TISSUE) of the tissues turns into a positive value.

In addition, the first IR pulse $IR_{BB}$ has been applied in the application region, which includes the upper stream side of the blood vessels and is larger than the imaging slab. For this reason, the longitudinal magnetization Mz(BB) of the blood flowing into the imaging slab from the outside after the application of the first IR pulse $IR_{BB}$ also shows a negative value because of the influence of the first IR pulse $IR_{BB}$. That is, blood flows from the outside of the imaging slab into the imaging slab with the T1 relaxation of the longitudinal magnetization Mz(BB).

Therefore, when the TI of the first IR pulse $IR_{BB}$ is appropriately set as shown in FIG. 3 (A), and also the application region of the first IR pulse $IR_{BB}$ is set large enough as shown in FIG. 4 (A) according to a flow velocity of the blood, the longitudinal magnetization Mz(TISSUE) of the tissues becomes a positive value and the longitudinal magnetization Mz(BB) of the blood becomes a negative value at the acquisition timing of the first MR signals $S_{BB}$. That is, the longitudinal magnetization Mz(BB) of the blood inside the imaging slab shows a negative value until blood, having the saturated longitudinal magnetization Mz, outside the application region of the first IR pulse $IR_{BB}$ flows into the imaging slab.

For this reason, when the TI of the first IR pulse $IR_{BB}$ is set short enough while the application region of the first IR pulse $IR_{BB}$ is set large enough, the first MR signals $S_{BB}$ of which MR signals from the tissues have positive values and MR signals from the blood have negative values can be acquired to generate BB image data. Moreover, as the TI is shorter, the absolute value of the longitudinal magnetization Mz(BB) of the blood and the absolute values of the MR signals from the blood can be larger.

On the other hand, the application region of the second IR pulse $IR_{WB}$ merely has a size covering the imaging slab and is narrower than the application region of the first IR pulse $IR_{BB}$ as shown in FIG. 4 (B). Therefore, blood, whose longitudinal magnetization Mz has saturated, flows into the imaging slab gradually without an effect by the second IR pulse $IR_{WB}$ after the application of the second IR pulse $IR_{WB}$. For this reason, the longitudinal magnetization Mz(WB) of the blood becomes a positive value earlier than the longitudinal magnetization Mz(TISSUE) of the tissues as shown in FIG. 3 (B).

Therefore, when the TI of the second IR pulse $IR_{WB}$ is set appropriately as shown in FIG. 3 (B), and also the application region of the second IR pulse $IR_{WB}$ is set to a region to the extent of covering the imaging slab as shown in FIG. 4 (B), the longitudinal magnetization Mz(TISSUE) of the tissues shows a positive value while the longitudinal magnetization Mz(WB) of the blood is also a positive value, at the acquisition timing of the second MR signals $S_{WB}$.

Moreover, as the TI of the second IR pulse $IR_{WB}$ is set shorter, the value of the longitudinal magnetization Mz(WB) of the blood becomes larger than the value of the longitudinal magnetization Mz(TISSUE) of the tissues. Therefore, when the TI of the first IR pulse $IR_{BB}$ and the TI of the second IR pulse $IR_{WB}$ are set to equivalent and short TIs as shown in FIG. 3, it becomes possible to acquire the second MR signals $S_{WB}$, whose MR signals from the tissues have positive values and MR signals from the blood also have positive values, for generating WB image data.

When the first MR signals $S_{BB}$ and the second MR signals $S_{WB}$ are acquired in the data acquisition conditions shown in FIG. 3 and FIG. 4, BB image data can be generated as T1W data which have an improved contrast. Moreover, when the TI of the first IR pulse $IR_{BB}$ and the TI of the second IR pulse $IR_{WB}$ are set to equivalent and short TIs, WB image data can be generated as T1W data, in which the tissues have been cancelled, by subtraction processing.

As a sequence for readout of MR signals for a T1W, a fast spin echo (FSE) sequence or an FFE sequence can be used. However, the FFE sequence is more preferable. The sequences for readout of the first MR signals $S_{BB}$ and the second MR signals $S_{WB}$ can be set in the sequence setting part 40B as mentioned above.

That is, the first example is data acquisition conditions in which the first IR pulse $IR_{BB}$ is applied in the first application region larger than an imaging area while the second IR pulse $IR_{WB}$ is applied in the second application region which is larger than the imaging area and narrower than the first application region. In this case, the first application region is set so that MR signals from blood flowing into the imaging area from the outside show negative values at acquisition timing of the first MR signals $S_{BB}$ for BB image data. Meanwhile, the second application region is set so that MR signals from blood flowing into the imaging area from the outside show positive values at acquisition timing of the second MR signals $S_{WB}$ for WB image data. Under such data acquisition conditions, each of BB image data and WB image data can be generated as T1W data.

In an example shown in FIG. 3, the TIs of the first IR pulse $IR_{BB}$ and the second IR pulse $IR_{WB}$ are set so that the longitudinal magnetization Mz(TISSUE) of tissues shows a positive value at timings of acquiring the first MR signals $S_{BB}$ and the second MR signals $S_{WB}$. However, the TIs of the first IR pulse $IR_{BB}$ and the second IR pulse $IR_{WB}$ may be set so that the first MR signals $S_{BB}$ and the second MR signals $S_{WB}$ are acquired at timing that the longitudinal magnetization Mz(TISSUE) of tissues shows a negative value, as mentioned above. In that case, short TIs can be set. In case of acquiring the first MR signals $S_{BB}$ and the second MR signals $S_{WB}$ at timing that the longitudinal magnetization Mz(TISSUE) of tissues shows a negative value, both MR signals from the tissues and MR signals from blood, which are included in the first MR signals $S_{BB}$, show negative values. However, in case of imaging tissues, whose signal difference from blood should be clarified, as background tissues, preferable data acquisition conditions are to acquire the first MR signals $S_{BB}$ at timing when MR signals from the tissues whose signal difference from blood should be clarified show positive values, as shown in FIG. 3 (A).

Next, the second example for applying one of the two first IR pulses, for generating BB image data, in a region larger than an imaging area, the other in a narrow region covering the imaging area, and both the two second IR pulses, for generating WB image data, in a narrow region covering the imaging area respectively in order to acquire each of the BB image data and the WB image data as T2W data or PDW data will be explained.

Figure 5:
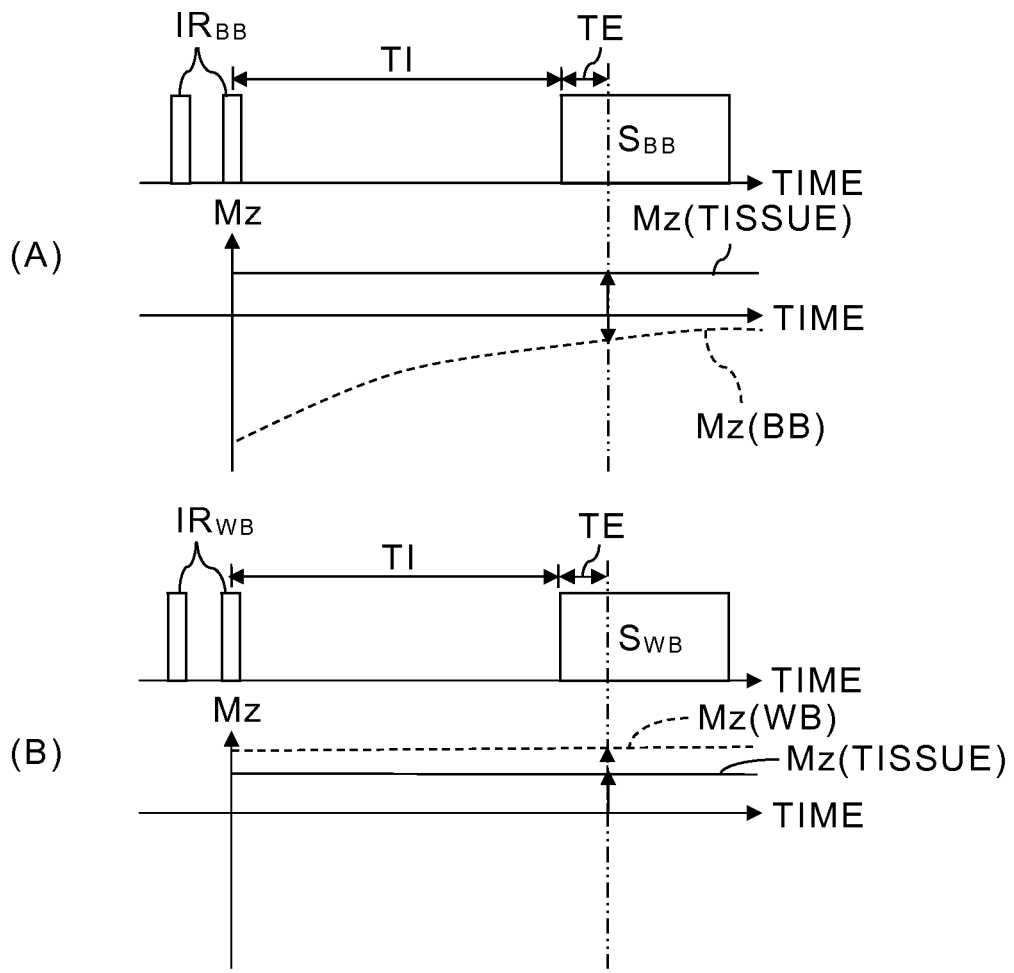
FIG. 5 is a chart showing application timing of two IR pulses for acquiring each of BB image data and WB image data as T2W data or PDW data.
Figure 6:
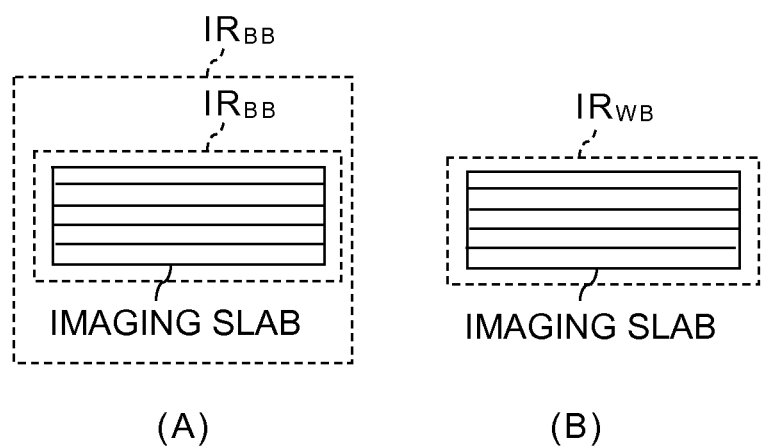
FIG. 6 is a view showing application areas of the first IR pulse and the second IR pulse shown in FIG. 5.

FIG. 5 is a chart showing application timing of two IR pulses for acquiring each of BB image data and WB image data as T2W data or PDW data. FIG. 6 is a view showing application areas of the first IR pulse and the second IR pulse shown in FIG. 5.

In (A) and (B) of FIG. 5, each horizontal axis represents time while the vertical axis of each graph represents longitudinal magnetizations Mz of blood and tissues. In FIG. 5, (A) shows application timing of the first two IR pulses $IR_{BB}$ for acquiring the first MR signals $S_{BB}$ for the BB image data and time changes of the longitudinal magnetization Mz (TISSUE) of the tissues and the longitudinal magnetization Mz (BB) of the blood flowing into an imaging slab, after applying the first IR pulses $IR_{BB}$. Meanwhile, (B) in FIG. 5 shows application timing of the second two IR pulses $IR_{WB}$ for acquiring the second MR signals $S_{WB}$ for the WB image data and time changes of the longitudinal magnetization Mz (TISSUE) of the tissues and the longitudinal magnetization Mz (BB) of the blood flowing into the imaging slab, after applying the second IR pulse $IR_{WB}$.

As shown in FIG. 5 (A), the first data acquisition conditions for performing a data acquisition sequence which acquires the first MR signals $S_{BB}$ with a TI and an appropriate TE after applying the first two IR pulses $IR_{BB}$ for the BB image data with an appropriate time interval can be set. Similarly, as shown in FIG. 5 (B), the second data acquisition conditions for performing a data acquisition sequence which acquires the second MR signals $S_{WB}$ with the TI and the appropriate TE after applying the second two IR pulses $IR_{WB}$ for the WB image data with the appropriate time interval can be set.

Furthermore, as shown in FIG. 6 (A), an application region by one of the first two IR pulses $IR_{BB}$ for the BB image data can be set as a region enough larger than an imaging slab which is an acquisition target of the first MR signals $S_{BB}$. Meanwhile, the other application region can be set as a region which covers the imaging slab and is narrower than the application region by the other first IR pulse $IR_{BB}$. Note that, an application order of the first IR pulses $IR_{BB}$ is arbitrary.

Then, the first IR pulse $IR_{BB}$ is applied twice in the imaging slab with a certain time interval. Therefore, each polarity of the longitudinal magnetization Mz(TISSUE) of the tissues and the longitudinal magnetization Mz of the blood inside the imaging slab inverts twice with the T1 relaxation according to the application interval of the first IR pulses $IR_{BB}$. As a result, both the longitudinal magnetization Mz(TISSUE) of the tissues and the longitudinal magnetization Mz of the blood inside the imaging slab becomes positive values immediately after the application of the two first IR pulses $IR_{BB}$.

On the other hand, the first IR pulse $IR_{BB}$ is applied once in the application region, for one of the first IR pulses $IR_{BB}$, outside of the imaging slab. Therefore, the polarities of the longitudinal magnetization Mz(TISSUE) of the tissues and the longitudinal magnetization Mz(BB) of the blood outside of the imaging slab invert. As a result, both the longitudinal magnetization Mz(TISSUE) of the tissues and the longitudinal magnetization Mz(BB) of the blood outside the imaging slab becomes negative values immediately after the application of the two first IR pulses $IR_{BB}$.

Then, blood, whose longitudinal magnetization Mz(BB) has become a negative value, flows from the outside of the imaging slab into the inside of the imaging slab with the T1 relaxation along the lapse of time. For this reason, the longitudinal magnetization Mz(TISSUE) of the tissues inside the imaging slab shows a positive value constantly while the longitudinal magnetization Mz(BB) of the blood flowing into the imaging slab gradually changes from a negative value to a positive value due to the T1 relaxation as shown in FIG. 5 (A).

Therefore, when the TI of the first IR pulses $IR_{BB}$ is appropriately set as shown in FIG. 5 (A), and also the larger one of the application regions of the first IR pulses $IR_{BB}$ is set large enough as shown in FIG. 6 (A) according to a flow velocity of the blood, the longitudinal magnetization Mz(TISSUE) of the tissues becomes a positive value while the longitudinal magnetization Mz(BB) of the blood, which has flown into the imaging slab, becomes a negative value at the acquisition timing of the first MR signals $S_{BB}$. That is, the longitudinal magnetization Mz(BB) of the blood inside the imaging slab shows a negative value until the blood, in which the longitudinal magnetization Mz has saturated, in the further outside of the larger one of the application regions of the first IR pulses $IR_{BB}$ flows into the imaging slab.

For this reason, when the TI of the first IR pulses $IR_{BB}$ is set appropriately while the larger side of the application regions of the first IR pulses $IR_{BB}$ is set large enough, the first MR signals $S_{BB}$, of which the MR signals from tissues have positive values and the MR signals from blood have negative values at the same time, can be acquired for generating the BB image data. Moreover, as the TI is shorter, the absolute value of the longitudinal magnetization Mz (BB) of the blood and the absolute values of the MR signals from the blood can be enlarged more.

On the other hand, as shown in FIG. 6 (B), each of the application regions of the two second IR pulses $IR_{WB}$ for the WB image data can be set to a region covering the imaging slab and narrower than the larger application region of the first IR pulse $IR_{BB}$. It is rational that a region equivalent to the narrower application region of the first IR pulse $IR_{BB}$ is set to the application regions of the two second IR pulses $IR_{WB}$.

Then, the second IR pulse $IR_{WB}$ is applied inside the imaging slab twice with a certain time interval. Therefore, the polarities of the longitudinal magnetization Mz(TISSUE) of the tissues and the longitudinal magnetization Mz of the blood inside the imaging slab invert twice, with the T1 relaxations according to the application interval of the second IR pulses $IR_{WB}$.

As a result, immediately after the application of the two second IR pulses $IR_{WB}$, each of the longitudinal magnetization Mz(TISSUE) of the tissues and the longitudinal magnetization Mz of the blood inside the imaging slab has not been saturated yet, and shows a positive value. That is, imperfect inversions of the longitudinal magnetizations Mz arise inside the imaging slab because of the application of the two second IR pulses $IR_{WB}$ with a predetermined application interval. Then, the longitudinal magnetization Mz(TISSUE) of the tissues and the longitudinal magnetization Mz of the blood decrease because of the imperfect inversions of the longitudinal magnetizations Mz.

On the other hand, the second IR pulses $IR_{WB}$ are not applied outside the imaging slab. Therefore, immediately after the application of the two second IR pulses $IR_{WB}$, both the longitudinal magnetization Mz(TISSUE) of the tissues and the longitudinal magnetization Mz (WB) of the blood outside the imaging slab are in saturated states, and show their positive maximums.

Then, the blood with the maximum longitudinal magnetization Mz(WB) flows from the outside of the imaging slab to the inside of the imaging slab, with the lapse of time. For this reason, the longitudinal magnetization Mz (TISSUE) of the tissues, which is in the non-saturated state and in the inside of the imaging slab, and the longitudinal magnetization Mz(WB) of the blood, which flows into the imaging slab and in the saturated state, show different positive values, as shown in FIG. 5 (B). In this case, the longitudinal magnetization Mz (WB) of the blood that flows into the inside of the imaging slab is constant regardless of a preset value of the TI.

Therefore, when the TI of the second IR pulses $IR_{WB}$ is set equivalent to the TI of the first IR pulses $IR_{BB}$ as shown in FIG. 5 (B), and both the application regions of the two second IR pulses $IR_{WB}$ are set to regions to the extent of covering the imaging slab as shown in FIG. 6 (B) at the same time, each of the longitudinal magnetization Mz(TISSUE) of the tissues and the longitudinal magnetization Mz(WB) of the blood shows a positive value at the acquisition timing of the second MR signals $S_{WB}$. For this reason, the second MR signals $S_{WB}$, whose MR signals from the tissues have positive values and MR signals from the blood also have positive values, can be acquired for generation of the WB image data.

When the first MR signals $S_{BB}$ and the second MR signals $S_{WB}$ are acquired in the data acquisition conditions shown in FIG. 5 and FIG. 6, the BB image data can be generated as T2W data or PDW data having an improved contrast. Moreover, when the TI of the first IR pulses $IR_{BB}$ and the TI of the second IR pulses $IR_{WB}$ are set to equivalent TIs, WB image data can be generated as T2W data or PDW data in which the tissues have been deleted by subtraction processing.

As a sequence for readout of MR signals for T2W or PDW, an FSE sequence or an echo planar imaging (EPI) sequence can be mentioned. When a repetition time (TR) is set to be long enough and a TE is set to be short, the BB image data and the WB image data can be generated as PDW data. On the other hand, the BB image data and the WB image data can be generated as T2W data by setting a TE to be long.

That is, the second example is data acquisition conditions, in which the first IR pulse $IR_{BB}$ is applied in each of the first application region, larger than an imaging area, and the second application region, larger than the imaging area and narrower than the first application region, with a predetermined time interval, while the second IR pulse $IR_{WB}$ is applied twice in the third application region larger than the imaging area and narrower than the first application region, with a predetermined time interval. In this case, the first application region is set so that MR signals from blood that has flowed from an outside into the imaging area show negative values at acquisition timing of the first MR signals $S_{BB}$ for BB image data. Moreover, the third application region is set so that MR signals from blood that has flowed from an outside into the imaging area show positive values at acquisition timing of the second MR signals $S_{WB}$ for WB image data. Therefore, the third application region is same as or different from the second application region. Moreover, it is rational that the predetermined time interval between the second IR pulses $IR_{WB}$ is set to be same as the predetermined time interval between the first IR pulses $IR_{BB}$. However, the predetermined time interval between the second IR pulses $IR_{WB}$ may be set to be different from the predetermined time interval between the first IR pulses $IR_{BB}$. Under such data acquisition conditions, BB image data and WB image data can be generated as T2W data or PDW data.

Next, the third example will be described. In the third example, BB image data and WB image data are acquired as T2W data or PDW data with applying a single IR pulse for generating the BB image data in a region of an upper stream side, of a blood flow, than an imaging area and applying no IR pulse for generating the WB image data.

Figure 7:
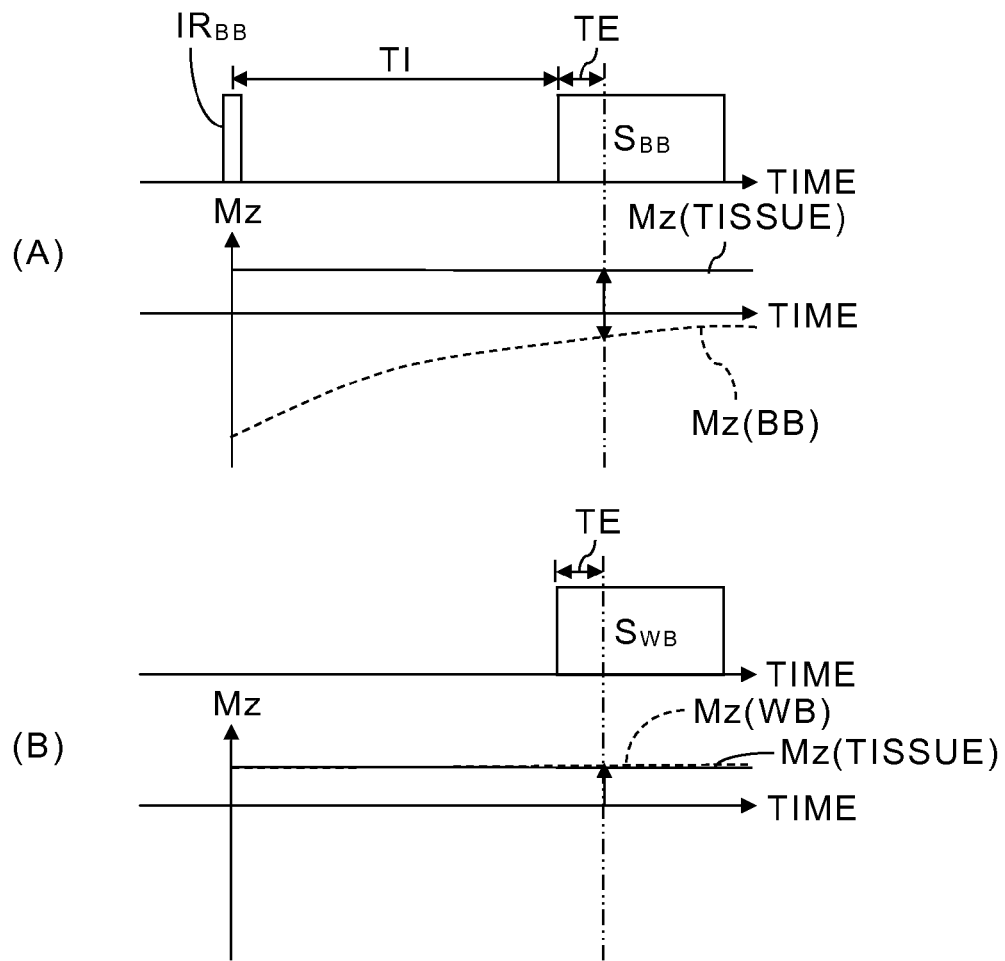
FIG. 7 is a chart showing application timing of a single IR pulse for acquiring each of BB image data and WB image data as T2W data or PDW data.
Figure 8:
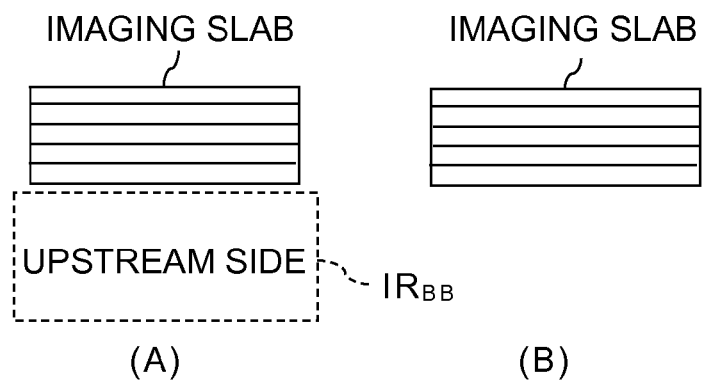
FIG. 8 is a view showing an application area of the IR pulse shown in FIG. 7.

FIG. 7 is a chart showing application timing of a single IR pulse for acquiring each of BB image data and WB image data as T2W data or PDW data. FIG. 8 is a view showing an application area of the IR pulse shown in FIG. 7.

In (A) and (B) of FIG. 7, each horizontal axis represents time while the vertical axis of each graph represents longitudinal magnetizations Mz of blood and tissues. In FIG. 7, (A) shows application timing of the IR pulse $IR_{BB}$ for acquiring the first MR signals $S_{BB}$ for the BB image data and time changes of the longitudinal magnetization Mz (TISSUE) of the tissues and the longitudinal magnetization Mz (BB) of the blood flowing into an imaging slab, after applying the IR pulse $IR_{BB}$. Meanwhile, (B) in FIG. 7 shows acquisition timing of the second MR signals $S_{WB}$ for the WB image data and time changes of the longitudinal magnetization Mz (TISSUE) of the tissues and the longitudinal magnetization Mz (BB) of the blood flowing into the imaging slab.

As shown in FIG. 7 (A), the first data acquisition conditions for performing a data acquisition sequence which acquires the first MR signals $S_{BB}$ with a TI and an appropriate TE after applying IR pulse $IR_{BB}$ for the BB image data can be set. Meanwhile, as shown in FIG. 7 (B), the second data acquisition conditions for performing a data acquisition sequence which acquires the second MR signals $S_{WB}$ for the WB image data with the appropriate TE without applying an IR pulse can be set.

Furthermore, as shown in FIG. 8 (A), an application region of the IR pulse $IR_{BB}$ for the BB image data can be set as a region in the upstreamer side of a blood flow than an imaging slab which is an acquisition target of the first MR signals $S_{BB}$. Meanwhile, as shown in FIG. 8 (B), no region other than the imaging slab is set for the WB image data.

Then, the polarities of the longitudinal magnetization Mz of the tissues and the longitudinal magnetization Mz(BB) of the blood, in the application region, of the IR pulse $IR_{BB}$, set outside the imaging slab, invert by the application of the IR pulse $IR_{BB}$. For this reason, the longitudinal magnetization Mz of the tissues and the longitudinal magnetization Mz(BB) of the blood, inside the application region of the IR pulse $IR_{BB}$ show negative values. On the other hand, the longitudinal magnetization Mz(TISSUE) of the tissues and the longitudinal magnetization Mz of the blood, inside the imaging slab, are under saturated conditions and show the positive maximums.

Then, the blood, of which the longitudinal magnetization Mz(BB) shows a negative value under the influence of the IR pulse $IR_{BB}$, inside the application region of the IR pulse $IR_{BB}$, flows into the imaging slab, with the T1 relaxation. For this reason, the longitudinal magnetization Mz(TISSUE) of the tissues inside the imaging slab shows a positive value constantly while the longitudinal magnetization Mz(BB) of the blood which flows into the imaging slab gradually changes from a negative value to a positive value due to the T1 relaxation, as shown in FIG. 7 (A).

Therefore, when the TI of the IR pulse $IR_{BB}$ is set appropriately as shown in FIG. 7 (A), and also the application region of the IR pulse $IR_{BB}$ is set to an appropriate position and range, according to a flow velocity of the blood, as shown in FIG. 8 (A), the longitudinal magnetization Mz(TISSUE) of the tissues show a positive value while the longitudinal magnetization Mz(BB) of the blood, which has flowed into the imaging slab, show a negative value, at the acquisition timing of the first MR signals $S_{BB}$. That is, the longitudinal magnetization Mz(BB) of the blood inside the imaging slab shows a negative value until the blood, of which the longitudinal magnetization Mz has been saturated in the further upper stream region than the application region of the IR pulse $IR_{BB}$, flows into the imaging slab.

For this reason, when the TI of the IR pulse $IR_{BB}$ is appropriately set and also the application region of the IR pulse $IR_{BB}$ is set to a sufficient range, the first MR signals $S_{BB}$ of which the MR signals from the tissues show positive values and the MR signals from the blood show negative values can be acquired for generating the BB image data.

On the other hand, the second MR signals $S_{WB}$ for the WB image data are acquired without an application of an IR pulse as shown in FIG. 7 (B) and FIG. 8 (B). Therefore, the second MR signals $S_{WB}$ are acquired in the state that both the longitudinal magnetization Mz(TISSUE) of the tissues and the longitudinal magnetization Mz(WB) of the blood show positive values. For this reason, the second MR signals $S_{WB}$ whose MR signals from the tissues show positive values and MR signals from the blood also show positive values can be acquired for generating the WB image data.

When the first MR signals $S_{BB}$ and the second MR signals $S_{WB}$ are acquired under the data acquisition conditions shown in FIG. 7 and FIG. 8, the BB image data can be generated as T2W data or PDW data having a favorable contrast. Moreover, when the acquisition timing of the first MR signals $S_{BB}$ and the acquisition timing of the second MR signals $S_{WB}$ are set to be similar, the WB image data can be generated as T2W data or PDW data in which the tissues have been deleted by subtraction processing.

That is, the BB image data and the WB image data can be generated as PDW data by an FSE sequence or an EPI sequence whose TE is set to be short. On the other hand, by an FSE sequence or an EPI sequence whose TE is set to be long, the BB image data and the WB image data can be generated as T2W data.

That is, the third example is data acquisition conditions in which the IR pulse $IR_{BB}$ for BB image data is applied in an application region outside an imaging area while the second MR signals $S_{WB}$ for WB image data are acquired without applying an IR pulse. In this case, the application region of the IR pulse $IR_{BB}$ for the BB image data is set so that MR signals from blood, that has flowed into the imaging area from an outside, have negative values at acquisition timing of the first MR signals $S_{BB}$ for the BB image data. Under such data acquisition conditions, the BB image data and the WB image data can be generated as T2W data or PDW data.

In the third example, two times inversions of the longitudinal magnetization Mz inside an imaging slab are not performed, which is different from the second example. For this reason, a decrease of longitudinal magnetization Mz due to an imperfect inversion of the longitudinal magnetization Mz does not arise. As a result, the SNR (signal to noise ratio) can be improved.

When data acquisition conditions are set so that the longitudinal magnetization Mz(TISSUE) of tissues recovers from a negative value to a positive value due to the T1 relaxation, after an application of at least one IR pulse, as the above mentioned first to third examples, the data acquisition conditions become conditions for acquisition of T1W data. On the other hand, when data acquisition conditions are set so that the longitudinal magnetization Mz(TISSUE) of tissues becomes almost constant after an application of at least one IR pulse, the data acquisition conditions become conditions for acquisition of T2W data or PDW data.

Each of the first to third examples shows a case in which a TI for BB image data and a TI for WB image data are set to TIs which can be considered to be same. However, a TI for BB image data and a TI for WB image data can also be set to different TIs, as mentioned above. When a TI for BB image data and a TI for WB image data are set to different TIs, image signals of background tissues are not canceled even when subtraction processing of image signals is performed for generating the WB image data. However, the WB image data in which blood has been depicted satisfactorily can be generated.

Moreover, data acquisition conditions to acquire both the first MR signals $S_{BB}$ for BB image data and the second MR signals $S_{WB}$ for WB image data after an application of a common IR pulse or common IR pulses can also be set.

Figure 9:
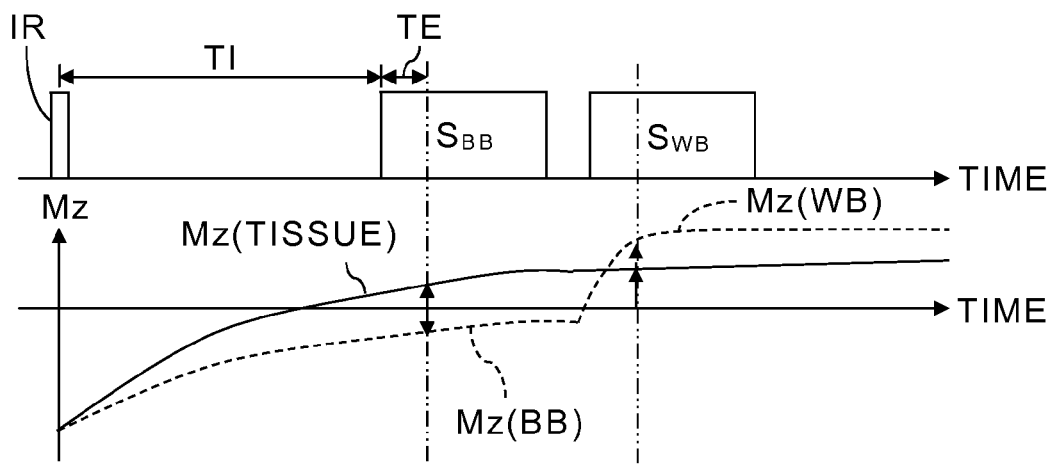
FIG. 9 is a chart showing conditions for acquiring both the first MR signals for BB image data and the second MR signals for WB image data by applying a common IR pulse.
Figure 10:
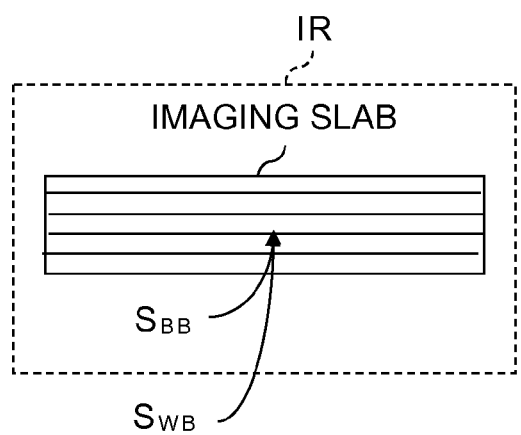
FIG. 10 is a view showing an application area of the IR pulse shown in FIG. 9.

FIG. 9 is a chart showing conditions for acquiring both the first MR signals $S_{BB}$ for BB image data and the second MR signals $S_{WB}$ for WB image data by applying a common IR pulse. FIG. 10 is a view showing an application area of the IR pulse shown in FIG. 9.

In FIG. 9, each horizontal axis shows time while the vertical axis of the graph shows the longitudinal magnetizations Mz of blood and tissues. FIG. 9 shows application timing of a common IR pulse for acquiring both the first MR signals $S_{BB}$ for the BB image data and the second MR signals $S_{WB}$ for the WB image data, respective acquisition timings of the first MR signals $S_{BB}$ and the second MR signals $S_{WB}$, and time changes of the longitudinal magnetization Mz (TISSUE) of the tissues and the longitudinal magnetization Mz of the blood in an imaging slab.

As shown in FIG. 9, data acquisition conditions can be set so that a data acquisition sequence, for applying a single IR pulse, and subsequently, acquiring both the first MR signals $S_{BB}$ for BB image data and the second MR signals $S_{WB}$ for WB image data after a TI with appropriate TEs, is performed. Furthermore, an application region of the IR pulse can be set to a region enough larger than an imaging slab which is an acquisition target of the first MR signals $S_{BB}$ and the second MR signals $S_{WB}$, as shown in FIG. 10.

Then, similarly to the example shown in FIG. 3 (A), when the TI of the IR pulse is appropriately set as shown in FIG. 9 and also the application region of the IR pulse is set large enough according to a flow velocity of blood as shown in FIG. 10, the longitudinal magnetization Mz(TISSUE) of the tissues shows a positive value while the longitudinal magnetization Mz(BB) of the blood shows a negative value, at acquisition timing of the first MR signals $S_{BB}$. That is, the longitudinal magnetization Mz(BB) of the blood in the imaging slab shows a negative value until the blood, of which the longitudinal magnetization Mz(WB) has been saturated, outside the IR pulse application region, flows into the imaging slab. Thereby, the first MR signals $S_{BB}$ which include the MR signals, having positive values, from the tissues and the MR signals, having negative values, from the blood can be acquired for generation of the BB image data.

After that, when the blood, of which the longitudinal magnetization Mz(WB) has been saturated, outside the IR pulse application region, flows into the imaging slab as shown in FIG. 10, the longitudinal magnetization Mz(WB) of the blood also becomes a positive value as shown in FIG. 9. Therefore, on the condition that acquisition timing of the second MR signals $S_{WB}$ is set appropriately, the second MR signals $S_{WB}$ which include the MR signals, having positive values, from the tissues and the MR signals, having positive values, from the blood can be acquired for generation of the WB image data as shown in FIG. 9.

When the first MR signals $S_{BB}$ and the second MR signals $S_{WB}$ are acquired under the data acquisition conditions as shown in FIG. 9 and FIG. 10, the BB image data can be generated as T1W data having an improved contrast. Moreover, the WB image data can be generated as T1W data in which the tissues have been suppressed by subtraction processing. As a sequence for readout of the MR signals, an FSE sequence or an FFE sequence can be used. Note that, when the first MR signals $S_{BB}$ and the second MR signals $S_{WB}$ are acquired after an application of a common IR pulse as exemplified in FIG. 9, the first MR signals $S_{BB}$ or both the first MR signals $S_{BB}$ and the second MR signals $S_{WB}$ may be acquired at timing that MR signals from tissues show negative values. That is, what is necessary is to acquire the first MR signals $S_{BB}$, of which MR signals from blood have negative values, and the second MR signals $S_{WB}$, of which MR signals from blood have positive values, which means whether MR signals from tissues have positive or negative values is arbitrary in the first MR signals $S_{BB}$ and the second MR signals $S_{WB}$.

In addition to the example shown in FIG. 9 and FIG. 10, conditions for applying an IR pulse twice in two application regions as shown in FIG. 6 (A) may be set. Alternatively, conditions for applying an IR pulse once in a region in the upper stream side of an imaging slab as shown in FIG. 8 (A) may also be set. In each case, when acquisition timing of the second MR signals $S_{WB}$ is set to a timing after the blood, of which the longitudinal magnetization Mz(WB) is in the saturated state and shows a positive value, has flowed into the imaging slab from an upper stream region of the IR pulse application region, both the first MR signals $S_{BB}$ including the MR signals, having negative values, from the blood and the second MR signals $S_{WB}$ including the MR signals, having positive values, from the blood can be acquired.

In this case, the BB image data and the WB image data can be generated as T2W data or PDW data by setting a TE. That is, after the application of a common IR pulse, both the first MR signals $S_{BB}$ and the second MR signals $S_{WB}$ for generating the BB image data and the WB image data as T2W data or PDW data can be acquired.

Acquisition of the first MR signals $S_{BB}$ and the second MR signals $S_{WB}$ for generating BB image data and WB image data can be also performed repeatedly, with setting an appropriate TR and changing at least one of a TI and a TE. That is, sets of the first MR signals $S_{BB}$ and/or sets the second MR signals $S_{WB}$ corresponding to at least one of multiple different TIs and multiple different TEs can be acquired.

In that case, it is possible to generate at least one of image data showing a T1 distribution, image data showing a T2 distribution, image data showing a permeability distribution of blood to tissues, and blood dynamic state image data, based on at least sets the first MR signals $S_{BB}$.

For example, when sets of MR signals corresponding to multiple different TIs are acquired, it becomes possible to generate dynamic image data showing hemodynamics. Therefore, when it is desired to acquire both BB image data and WB image data as blood dynamic state image data, data conditions for acquiring sets of the first MR signals $S_{BB}$ and sets of the second MR signals $S_{WB}$ corresponding to multiple different TIs should be set. In this case, blood dynamic state image data can be acquired as VWI data and ASL (arterial spin labeling) MRA image data. The ASL image data is perfusion image data of blood acquired by applying at least one IR pulse to label spins of blood.

For a practical example, data acquisition conditions for acquiring both sets of the first MR signals $S_{BB}$ and sets of the second MR signals $S_{WB}$ with a same combination of TIs, i.e. data acquisition conditions for acquiring both the first MR signals $S_{BB}$ and the second MR signals $S_{WB}$ with a same TI changing for every TR, can be set.

However, it may be important to generate blood dynamic state image data as VWI data, depending on a diagnostic purpose. In such a case, what is necessary is to set data acquisition conditions for acquiring the second MR signals $S_{WB}$, corresponding to WB image data, with a single TI and repeatedly acquiring the first MR signals $S_{BB}$, corresponding to BB image data, with multiple TIs, i.e., data acquisition conditions for acquiring the second MR signals $S_{WB}$ corresponding to the single TI and multiple sets of the first MR signals $S_{BB}$ corresponding to the multiple TIs. Alternatively, data acquisition conditions for acquiring the second MR signals $S_{WB}$ repeatedly with multiple TIs fewer than the multiple TIs for acquiring the first MR signals $S_{BB}$, i.e., data acquisition conditions in which the number of TIs for acquiring sets of the second MR signals $S_{WB}$ is fewer than the number of TIs for acquiring sets of the first MR signals $S_{BB}$, may be set.

Moreover, in a case of generating VWI data, it is important to acquire indexes indicating whether a plaque easily exfoliates from a blood vessel wall or the like, and to judge an aspect of the plaque. Examples of index, whose usability for a judgment in aspect of a plaque has been reported, include T1, T2, apparent diffusion coefficients (ADC), and the like.

Accordingly, data acquisition conditions can be set so as to generate image data showing a distribution of an index for aspect judgment of a plaque. For example, T1 distribution image data in which T1 values are mapped in spatial positions can be calculated by an approximation method, such as curve fitting, for MR signals corresponding to at least two different TIs. On the other hand, T2 distribution image data in which T2 values are mapped in spatial positions can be calculated by an approximation method, such as curve fitting, for MR signals corresponding to at least two different TEs.

Therefore, in a case of acquiring T1 distribution image data, multiple TIs should be set. On the other hand, in a case of acquiring T2 distribution image data, multiple TEs should be set. Surely, in order to acquire both T1 distribution image data and T2 distribution image data, multiple TIs and TEs may also be set.

Moreover, a T2 may change depending on a value of TI. Therefore, even in a case of acquiring only T2 distribution image data, it may be useful to generate T2 distribution image data for every TI, with setting multiple TIs and TEs. Alternatively, as long as a change amount of T2 is negligible, data acquisition conditions to acquire MR signals repeatedly with changing only a TE may be set by setting a typical TI.

Especially, an amount of change in T2 between different TIs varies depending on a permeability of blood into tissues. Therefore, multiple frames of T2 distribution image data corresponding to multiple different TIs may contribute to understanding an aspect of plaque. That is, it becomes possible to generate permeability distribution image data, useful to understanding an aspect of plaque, based on a change amount in T2 between different TIs. In this case, perfusion image data sets, of blood in a blood vessel part or tissues, corresponding to multiple TIs can also be acquired. Furthermore, it becomes possible to generate parameter distribution image data, in which an arbitrary parameter, such as a blood flow (BF) or a blood volume (BV), has been mapped.

As mentioned above, data acquisition conditions for acquiring at least multiple sets of the first MR signals $S_{BB}$ corresponding to at least one of multiple different TIs and multiple different TEs can be set in the imaging condition setting unit 40. In that case, data acquisition conditions for acquiring multiple sets of the second MR signals $S_{WB}$ corresponding to at least one of multiple different TIs and multiple different TEs can be also set according to diagnostic image data as a generation object.

Each of the first MR signals $S_{BB}$ and the second MR signals $S_{WB}$ corresponding to a single or multiple TIs may be segmented in units of a predetermined area in a k-space so that respective parts of the segmented signals can be acquired alternately in terms of time. Specifically, each of the first MR signals $S_{BB}$ and the second MR signals $S_{WB}$ corresponding to a common TI can be acquired under data acquisition conditions not only by one time of data acquisition but by multiple times of data acquisition. In that case, the first MR signals $S_{BB}$ and the second MR signals $S_{WB}$ corresponding to a common TI can be alternately acquired. When the first MR signals $S_{BB}$ and the second MR signals $S_{WB}$ are alternately acquired, time phase differences between the first MR signals $S_{BB}$ and the second MR signals $S_{WB}$, each arranged in a k-space, can be reduced compared with a case where the first MR signals $S_{BB}$ and the second MR signals $S_{WB}$ are acquired non-alternately.

Figure 11:
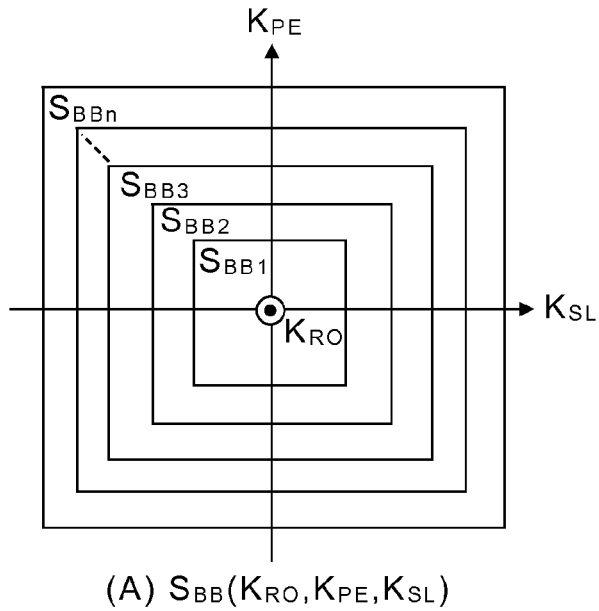
FIG. 11 is graphs showing an example of segmenting each the first MR signals for BB image data and the second MR signals for WB image data into signal trains in plural regions of the k-space.
Figure 11:
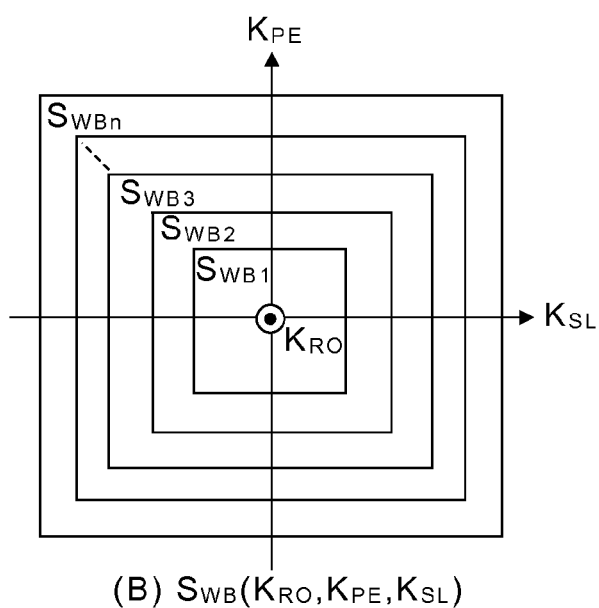

FIG. 11 is graphs showing an example of segmenting each of the first MR signals $S_{BB}$ for BB image data and the second MR signals $S_{WB}$ for WB image data into signal trains in plural regions of the k-space.

In (A) and (B) of FIG. 11, each vertical axis represents position $K_{PE}$ in a PE (phase encode) direction in the k-space, each horizontal axis represents position $K_{SL}$ in a slice direction in the k-space, and each axis orthogonal to the plane of paper represents position $K_{RO}$ in an RO (readout) direction in the k-space, respectively. Moreover, FIG. 11 (A) shows the k-space where the first MR signals $S_{BB}(K_{RO}, K_{PE}, K_{SL})$ for 3D (three dimensional) BB image data are arranged while FIG. 11 (B) shows the k-space where the second MR signals $S_{WB}(K_{RO}, K_{PE}, K_{SL})$ for 3D WB image data are arranged.

As shown in FIG. 11 (A), the first MR signals $S_{BB}(K_{RO}, K_{PE}, K_{SL})$ can be segmented in the $K_{PE}$ direction and the $K_{SL}$ direction into multiple 3D regions, according to a distance from the center of the k-space. In this case, the segment including the center of the k-space is a cuboid region while each of the other segments is a rectangular tubular region. Similarly, as shown in FIG. 11 (B), the second MR signals $S_{WB}(K_{RO}, K_{PE}, K_{SL})$ can also be segmented in the $K_{PE}$ direction and the $K_{SL}$ direction into multiple 3D regions, according to a distance from the center of the k-space.

In the illustrated example, the k-space corresponding to the first MR signals $S_{BB}(K_{RO}, K_{PE}, K_{SL})$ has been segmented into n segments. For this reason, the first MR signals $S_{BB}(K_{RO}, K_{PE}, K_{SL})$ have been segmented into the first n MR signal trains $S_{BB1}, S_{BB2}, S_{BB3}, \ldots, S_{BBn}$. Similarly, the k-space corresponding to the second MR signals $S_{WB}(K_{RO}, K_{PE}, K_{SL})$ has also been segmented into n segments. For this reason, the second MR signals $S_{WB}(K_{RO}, K_{PE}, K_{SL})$ have been segmented into the second n MR signal trains $S_{WB1}, S_{WB2}, S_{WB3}, \ldots, S_{WBn}$.

Figure 12:
FIG. 12 is a time chart which shows an acquisition order of the signal trains in the segments shown in FIG. 11.

FIG. 12 is a time chart which shows an acquisition order of the signal trains in the segments shown in FIG. 11.

In FIG. 12, the horizontal axis represents time. As shown in FIG. 12, the first n MR signal trains $S_{BB1}, S_{BB2}, S_{BB3}, \ldots,$ and $S_{BBn}$, and the second n MR signal trains $S_{WB1}, S_{WB2}, S_{WB3}, \ldots,$ and $S_{WBn}$ can be temporally alternately acquired. As a result, two sets of k-space data for the BB image data and the WB image data as shown in FIG. 11 can be acquired.

In this case, data acquisition conditions can be set so as to acquire one signal train $S_{BBi}$ (i=1, 2, 3, ..., n) of the first n MR signal trains $S_{BB1}, S_{BB2}, S_{BB3}, \ldots, S_{BBn}$ and one signal train $S_{WBi}$ of the second n MR signal trains $S_{WB1}, S_{WB2}, S_{WB3}, \ldots, S_{WBn}$, after an application of a common IR pulse as shown in FIG. 9. That is, data acquisition conditions can be set so that an IR pulse is applied repeatedly with a predetermined TR to alternately acquire a part of the first MR signals $S_{BB}$ and a part of the second MR signals $S_{WB}$ between the IR pulse applications. In this case, the number of application times of an IR pulse can be decreased and a data application period can be shortened.

Alternatively, data acquisition conditions may be set so that either a certain signal train $S_{BBi}$ (i=1, 2, 3, ..., n) of the first n MR signal trains $S_{BB1}, S_{BB2}, S_{BB3}, \ldots, S_{BBn}$ or a certain signal train $S_{WBi}$ of the second n MR signal trains $S_{WB1}, S_{WB2}, S_{WB3}, \ldots, S_{WBn}$ is acquired between IR pulse applications. In this case, data acquisition conditions may be set so as to alternately repeat data acquisitions shown in (A) and (B) of FIG. 3, FIG. 5, or FIG. 7. Therefore, TIs can be set to be same between the first MR signal trains $S_{BB1}, S_{BB2}, S_{BB3}, \ldots, S_{BBn}$ and the second MR signal trains $S_{WB1}, S_{WB2}, S_{WB3}, \ldots, S_{WBn}$.

Note that, the number of acquisition times of the first MR signals $S_{BB}$ is same as that of the second MR signals $S_{WB}$ when the number of TIs for acquiring the first MR signals $S_{BB}$ is same as that for acquiring the second MR signals $S_{WB}$. Therefore, all the first MR signals $S_{BB}$ and all the second MR signals $S_{WB}$ can be segmented into the first MR signal trains $S_{BB1}, S_{BB2}, S_{BB3}, \ldots, S_{BBn}$ and the second MR signal trains $S_{WB1}, S_{WB2}, S_{WB3}, \ldots, S_{WBn}$ respectively so that they can be acquired alternately in time as shown in FIG. 12.

On the other hand, when the number of TIs for acquiring the first MR signals $S_{BB}$ differs from that for acquiring the second MR signals $S_{WB}$, the number of acquisition times of the first MR signals $S_{BB}$ also differs from that of the second MR signals $S_{WB}$. Accordingly, a part of MR signal trains acquired with the more TIs can be acquired before or after interleaved acquisitions as shown in FIG. 12.

Alternatively, all the first MR signals $S_{BB}$ and all the second MR signals $S_{WB}$ can be also acquired by interleaved acquisitions as shows in FIG. 12 by changing the numbers of signals included in MR signal trains acquired between IR pulse applications. Specifically, even in a case where the number of TIs for acquiring the first MR signals $S_{BB}$ differs from that for acquiring the second MR signals $S_{WB}$, the number of MR signal trains composing the first MR signals $S_{BB}$ can be set to be same as the number of MR signal trains composing the second MR signals $S_{WB}$ by adjusting the numbers of signals included in the MR signal trains.

By cooperating with hardware including the static field magnet 21, the shim coil 22, the gradient coil 23, and the RF coils 24, the imaging condition setting unit 40, having the above mentioned functions, of the computer 32, functions as a data acquisition part configured to acquire the first MR signals $S_{BB}$, whose MR signals from tissues show positive values while MR signals from blood show negative values, and the second MR signals $S_{WB}$, whose MR signals from blood show positive values, from a same imaging region of an object P, by applying at least one IR pulse under application conditions according to relaxation times of blood and tissues. However, the data acquisition part may be configured by other elements as long as the same functions are provided.

On the other hand, the data processing unit 41 of the computer 32 functions as a data processing part which generates MR image data based on MR signals. Specifically, the data processing unit 41 has a function to obtain MR signals, acquired by an imaging scan under the imaging conditions set up in the imaging condition setting unit 40, from the sequence controller 31 to arrange the obtained MR signals in a k-space formed in the k-space data storage part 42; a function to take k-space data from the k-space data storage part 42 to reconstruct image data by image reconstruction processing including a FT (Fourier transform); a function to write the image data, obtained by the reconstruction, in the image data storage part 43; and a function to apply required image processing of image data taken from the image data storage part 43 to display the image data on the display unit 34.

In particular, the data processing unit 41 has a function to generate BB image data and WB image data based on the first MR signals $S_{BB}$ and the second MR signals $S_{WB}$. In addition, the data processing unit 41 has a function to generate quantitative image data, such as T1 distribution image data, T2 distribution image data, permeability distribution image data, or distribution image data of a blood flow parameter, based on the first MR signals $S_{BB}$ and/or the second MR signals $S_{WB}$ which were acquired with setting at least one of a TI and a TE to plural values.

The BB image generation part 41A of the data processing unit 41 has a function to generate BB image data using the first MR signals $S_{BB}$ as original data. The BB image data can be generated by FT of the first MR signals $S_{BB}$ to generate the first real space signals $V_{BB}$, a phase correction of the first real space signals $V_{BB}$, and real part extraction processing for generating an image using real parts Real($V_{BB.cor}$) of the first real space signals $V_{BB.cor}$, which are complex signals, after the phase correction, as signal values.

BB image data generated by data processing including the real part extraction processing performed as a part of such the real part imaging become MRA image data in which blood flowing inside blood vessels is depicted blackly as regions showing lower signals than that in background tissues. For this reason, BB image data can be provided for a diagnosis as VWI image data $I_{BB-VWI}$.

For example, when the first MR signals $S_{BB}$ have been acquired under the first data acquisition conditions exemplified by FIG. 3 and FIG. 4, BB-VWI image data $I_{BB-VWI}$ can be acquired as T1W data in which signals corresponding to blood have negative values and signals corresponding to tissues have positive values, as mentioned above. On the other hand, in a case where the first MR signals $S_{BB}$ have been acquired under the second data acquisition conditions exemplified by FIG. 5 and FIG. 6 or the third data acquisition conditions exemplified by FIG. 7 and FIG. 8, BB-VWI image data $I_{BB-VWI}$ can be acquired as T2W data or PDW data in which signals corresponding to blood have negative values and signals corresponding to tissues have positive values, as mentioned above.

Note that, when the first MR signals $S_{BB}$ have been acquired under conditions that both MR signals from blood and MR signals from tissues show negative values, BB image data can also be generated as amplitude image data by the magnitude extraction processing for generating an image using absolute values of real space signals obtained based on the first MR signals $S_{BB}$, instead of real part imaging. In that case, WB image data may be generated by black and white inversion processing of the BB image data. However, when BB image data are generated by imaging real parts Real($V_{BB.cor}$) of the first real space signals $V_{BB.cor}$ by real part imaging, regardless of whether MR signals from tissues show positive values or negative values, the BB image data can be generated without determining a positive/negative sign of the MR signals from the tissues.

In real part imaging, it is required to correct phases of real space signals, shifted due to the nonuniformity of the static magnetic field. This enables the real part components, having values according to amplitudes, of real space signals to be imaged. Therefore, it is important for the phase correction to use phase data which can be considered as a phase distribution, of background tissues, according to the nonuniformity of the static magnetic field.

Accordingly, the phase correction of the first real space signals $V_{BB}$ generated based on the first MR signals $S_{BB}$ can be performed based on phase data calculated based on the second MR signals $S_{WB}$ in which both MR signals from blood and MR signals from tissues show positive values. Specifically, a phase distribution which can be considered as a phase distribution, of background tissues, shifted due to the nonuniformity of the static magnetic field can be calculated based on the second MR signals $S_{WB}$ in which both MR signals from blood and MR signals from tissues show positive values, and the phase correction of the first MR signals $S_{BB}$ can be performed using the phase distribution calculated based on the second MR signals $S_{WB}$. That is, BB image data can be generated with the phase correction based on the second MR signals $S_{WB}$.

Moreover, in a case where multiple sets of the first MR signals $S_{BB}$ corresponding to multiple different TIs have been acquired, BB-VWI image data $I_{BB-VWI}$ can be acquired as blood dynamic state image data in the BB image generation part 41A, as mentioned above. That is, multiple frames of BB-VWI image data $I_{BB-VWI}$ can be generated as dynamic image data in the TI axis direction.

The WB image generation part 41B has a function to generate WB image data using the second MR signals $S_{WB}$ as original data. The WB image data can be generated by FT of the second MR signals $S_{WB}$ to generate the second real space signals $V_{WB}$ and magnitude extraction processing for generating an image using absolute values $|V_{WB}|$, showing amplitudes of the second real space signals $V_{WB}$ which are complex signals, as signal values.

In this case, when VWI image data $I_{BB-VWI}$ are subtracted from absolute values $|V_{WB}|$ of the second real space signals $V_{WB}$, WB-MRA image data $I_{WB-MRA}$ in which background tissues have been favorably suppressed can be generated. That is, WB-MRA image data $I_{WB-MRA}$ can be generated as image data, in which the depiction of tissues has been suppressed while blood has been depicted, by data processing including subtraction processing between image data generated based on the second MR signals $S_{WB}$ and image data generated based on the first MR signals $S_{BB}$.

Especially, when the TI for acquiring the first MR signals $S_{BB}$ is equivalent to the TI for acquiring the second MR signals $S_{WB}$, image signal components, corresponding to background tissues, which have become equivalent, are cancelled by subtraction processing. For this reason, WB-MRA image data $I_{WB-MRA}$, in which the background has been deleted and the CNR has been improved, can be generated. Surely, WB image data may also be generated using the second MR signals $S_{WB}$ as original data, without subtraction processing.

Thus, WB image data can be generated based on only the second MR signals $S_{WB}$ or both the first MR signals $S_{BB}$ and the second MR signals $S_{WB}$. Moreover, in a case where sets of the second MR signals $S_{WB}$ corresponding to at least multiple different TIs have been acquired, WB image data can be acquired as blood dynamic state image data in the WB image generation part 41B, as mentioned above. That is, multiple frames of WB image data can be generated as dynamic image data in the TI axis direction. Note that, in a case of performing subtraction processing in order to generate WB-MRA image data $I_{WB-MRA}$, what is necessary is to subtract common VWI image data $I_{BB-VWI}$ corresponding to a single TI or multiple frames of VWI image data $I_{BB-VWI}$ corresponding to multiple TIs from multiple frames of WB image data.

The quantitative image generation part 41C has a function to generate the above-mentioned quantitative image data, such as T1 distribution image data, T2 distribution image data, distribution image data of a permeability, or distribution image data of a parameter like a BF or a BV, based on MR signals repeatedly acquired with changing at least one of the TI and the TE. The quantitative image data can be generated based on one or both of multiple sets of the first MR signals $S_{BB}$ and multiple sets of the second MR signals $S_{WB}$, as mentioned above. Note that, in order to generate T1 distribution image data, real part extraction processing is required so that MR signals can have negative values.

Next, an operation and action of the magnetic resonance imaging apparatus 20 will be described.

Figure 13:
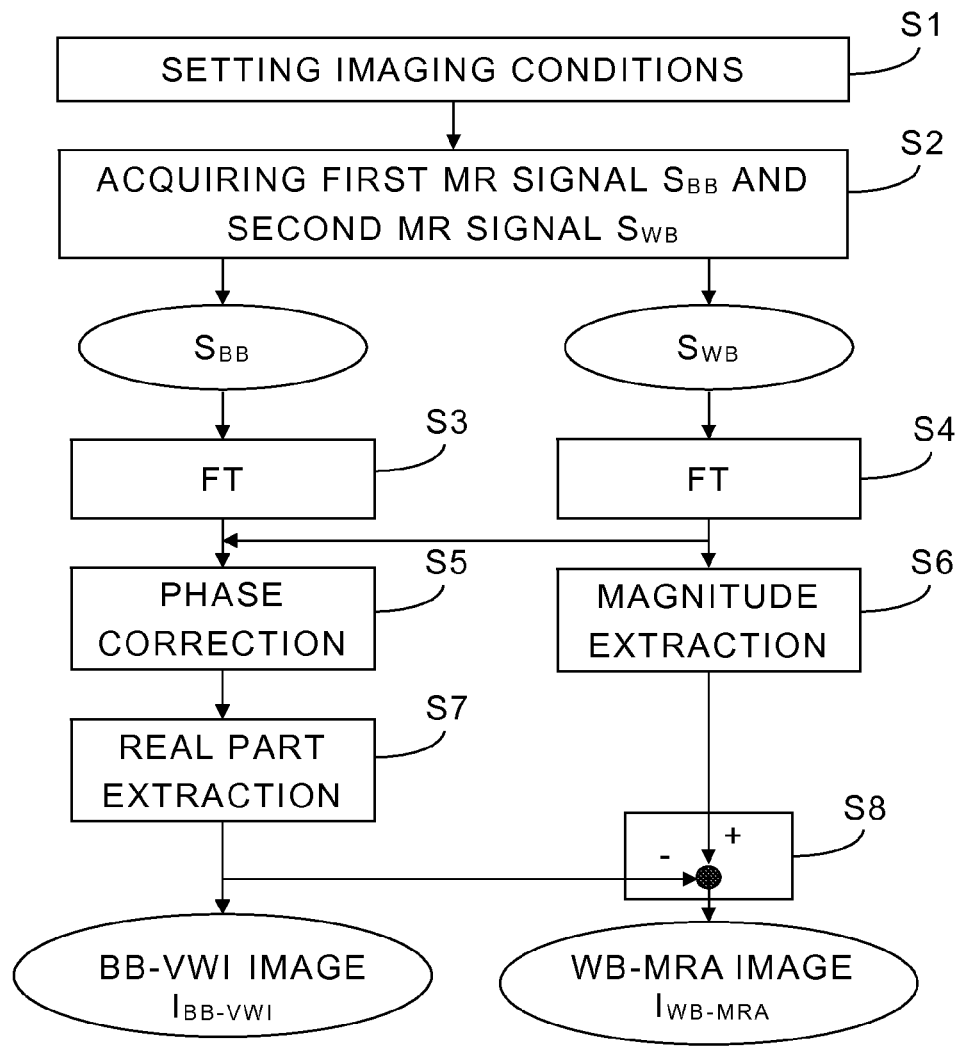
FIG. 13 is a flow chart which shows a flow for acquiring BB image data and WB image data of an imaging area of an object by the magnetic resonance imaging apparatus shown in FIG. 1.

FIG. 13 is a flow chart which shows a flow for acquiring BB image data and WB image data of an imaging area of an object P by the magnetic resonance imaging apparatus 20 shown in FIG. 1.

Firstly, in Step S1, imaging conditions are set in the imaging condition setting unit 40. Specifically, imaging conditions for an imaging scan are set so that the first MR signals $S_{BB}$, whose MR signals from blood show negative values, for generating BB image data and the second MR signals $S_{WB}$, whose MR signals from blood show positive values, for generating WB image data are respectively acquired from an imaging region by applying at least one IR pulse under application conditions according to at least the relaxation time of the blood.

As a concrete example, TEs, region segmentations in the k-spaces, readout sequences, and IR pulse application conditions, including TIs, the number of pulses, and application regions, as shown by FIG. 3 to FIG. 12, are set as data acquisition conditions for the first MR signals $S_{BB}$ and the second MR signals $S_{WB}$. Note that, application conditions of IR pulses are set in the IR pulses setting part 40A while readout sequences of MR signals are set in the sequence setting part 40B.

On the other hand, the object P is set to the bed 37, and a static magnetic field is generated at an imaging area of the magnet 21 (a superconducting magnet) for static magnetic field excited by the static-magnetic-field power supply 26. Further, the shim-coil power supply 28 supplies current to the shim coil 22, thereby uniformizing the static magnetic field generated at the imaging area.

Next, in Step S2, elements, including the sequence controller 31 and the static field magnet 21, of the magnetic resonance imaging apparatus 20 for performing a scan acquires the first MR signals $S_{BB}$ and the second MR signals $S_{WB}$ according to the imaging conditions set in the imaging condition setting unit 40.

Specifically, the input device 33 sends instruction of starting an imaging scan to the imaging condition setting unit 40. Therefore, the imaging condition setting unit 40 outputs the imaging conditions including a pulse sequence to the sequence controller 31. Then, the sequence controller 31 drives the gradient power supply 27, the transmitter 29, and the receiver 30 in accordance with the imaging conditions including the pulse sequence, thereby generating a gradient magnetic field at the imaging area having the set object P, and further generating RF signals from the RF coil 24.

Consequently, the RF coil 24 receives MR signals generated due to the nuclear magnetic resonance in the object P. Then, the receiver 30 receives the MR signals from the RF coil 24 to perform predetermined signal processing including A/D conversion. The receiver 30 outputs the MR signals, which have become digital signals, to the sequence controller 31. Furthermore, the sequence controller 31 outputs the MR signals to the computer 32.

As a result, the first MR signals $S_{BB}$ and the second MR signals $S_{WB}$ are output to the computer 32. Then, the BB image generation part 41A of the data processing unit 41 arranges the first MR signals $S_{BB}$ sequentially in the k-space for the BB image data formed in the k-space data storage unit 42. Meanwhile, the WB image generation part 41B arranges the second MR signals $S_{WB}$ sequentially in the k-space for the WB image data formed in the k-space data storage unit 42. Thereby, the set of k-space data for the BB image data and the set of k-space data for the WB image data are obtained.

Next, in Step S3, the BB image generation part 41A performs an FT of the first MR signals $S_{BB}$ shown by the formula (1). As a result, the first real space signals $V_{BB}$ are generated.

$$V_{BB}=FT(S_{BB}) \tag{1}$$

On the other hand, in Step S4, the WB image generation part 41B performs an FT of the second MR signals $S_{WB}$ shown by the formula (2). As a result, the second real space signals $V_{WB}$ are generated.

$$V_{WB}=FT(S_{WB}) \tag{2}$$

Next, in Step S5, the BB image generation part 41A performs a phase correction of the first real space signals $V_{BB}$ by the calculation shown by the formula (3). That is, phase correction processing of the first real space signals $V_{BB}$, using phase data acquired as a phase distribution of the second real space signals $V_{WB}$, is performed. As a result, the first real space signals $V_{BB.cor}$ after the phase correction are generated.

$$V_{BB.cor}=V_{BB}*\{Conj(V_{WB})/|V_{WB}|\} \tag{3}$$

wherein Conj( ) in the formula (3) is a function which outputs the complex conjugate.

On the other hand, in Step S6, the WB image generation part 41B performs magnitude extraction processing of the second real space signals $V_{WB}$ by the calculation shown by the formula (4). Thereby, the WB image data $I_{WB}$ are generated.

$$I_{WB}=|V_{WB}| \tag{4}$$

On the other hand, in Step S7, the BB image generation part 41A performs real part extraction processing, of the first real space signals $V_{BB.cor}$ after the phase correction, by the calculation shown by the formula (5). Thereby, BB-VWI image data $I_{BB-VWI}$, in which the blood has been depicted blackly with low signal values while the background tissues including blood vessel walls have been depicted whitely with high signal values, are generated.

$$I_{BB-VWI}=\text{Real}(V_{BB.cor}) \tag{5}$$

wherein Real( ) in the formula (5) is a function which outputs the real part of a complex number.

Furthermore, subtraction processing in Step S8 can be performed in the WB image generation part 41B, as needed. The subtraction processing is expressed by the formula (6). As a result, WB-MRA image data $I_{WB-MRA}$, in which the background tissues are suppressed while the blood is selectively depicted whitely with high signal values, are generated.

$$I_{WB-MRA}=I_{WB}-I_{BB-VWI} \tag{6}$$

Thus, both the BB-VWI image data $I_{BB-VWI}$ and the WB-MRA image data $I_{WB-MRA}$ can be provided for a diagnosis. When sets, of the first MR signals $S_{BB}$ and the second MR signals $S_{WB}$, corresponding to plural TIs have been acquired, each of BB-VWI image data $I_{BB-VWI}$ and WB-MRA image data $I_{WB-MRA}$ can be acquired as blood flow dynamic state image data.

Furthermore, in a case where at least one of the first MR signals $S_{BB}$ and the second MR signals $S_{WB}$ have been repeatedly acquired with changing one or both of the TI and the TE, T1 distribution image data, T2 distribution image data, permeability distribution image data, distribution image data of a parameter, such as a BF or a BV, or the like can be generated as quantitative image data for a diagnosis, based on one or both of the multiple sets of the first MR signals $S_{BB}$ and the multiple sets of the second MR signals $S_{WB}$, in the quantitative image generation part 41C.

That is, the above mentioned magnetic resonance imaging apparatus 20 is configured to appropriately set application conditions, such as a TI and an application region, of an IR pulse or IR pulses and perform real part imaging, as necessary, in order to acquire both BB image data and WB image data by one imaging scan.

For this reason, according to the magnetic resonance imaging apparatus 20, BB image data and WB image data are efficiently acquirable by a less number of imaging times and in a shorter imaging period. Especially, when real part imaging is performed with applying an IR pulse or IR pulses, MR signals from blood can be suppressed satisfactorily, compared with the case where absolute value image data are generated by applying saturation pulses or multiple IR pulses to suppress MR signals from blood. For this reason, BB-VWI image data can be acquired with a CNR better than before.

Furthermore, when the TI or TIs for the first MR signals $S_{BB}$ are set to be same as the TI or TIs for the second MR signals $S_{WB}$, WB image data in which background tissues have been deleted can be generated by subtraction processing which subtracts BB image data from WB image data. For this reason, a CNR of WB image data can be also improved.

In addition, the magnetic resonance imaging apparatus 20 can also generate a quantitative image on which a parameter, such as a T1, a T2, a BF, a BV, or a permeability, has been mapped. Thereby, a diagnostic ability for a plaque or the like can be improved.

On the contrary, according to the conventional blood vessel suppression method for applying saturation pulses to suppress MR signals from blood, the suppression effect is not fully attained in many cases. Moreover, according to the conventional MRA that performs imaging of amplitudes of MR signals, each MR signal from blood shows zero at the lowest. For this reason, it is difficult to distinguish a plaque as a low signal region. As a result, an additional acquisition of a WB image by the TOF method has been occasionally needed, conventionally.

On the contrary, according to the magnetic resonance imaging apparatus 20, an acquisition of WB image by the TOF method is not always required, and WB image data can be effectively used for a phase correction of BB image data. For this reason, the number of imaging times and an imaging time can be reduced, compared to the conventional method.

Second Embodiment

In a magnetic resonance imaging apparatus in the second embodiment, a data acquisition method of MR signals and a data processing method for generating MRA image data differ from those of the magnetic resonance imaging apparatus 20 in the first embodiment. Specifically, the magnetic resonance imaging apparatus in the second embodiment is configured to be able to perform a data acquisition of MR signals with applying at least one IR pulse under an AFI (Asymmetric Fourier Imaging) method and generate BB image data by real part imaging.

The AFI method is a method for sampling MR data so as to be asymmetric in the wavenumber direction in the k-space, and reconstructing MR image data after performing a phase correction of the sampling data using a phase distribution estimated based on the sampled self data.

According to the AFI method, MR image data equivalent to MR image data generated from MR data sampled symmetrically in the k-space can be generated. For this reason, a data acquisition time can be shortened.

Other configurations and functions of the magnetic resonance imaging apparatus in the second embodiment are same as those of the magnetic resonance imaging apparatus 20 in the first embodiment. Therefore, only a functional block diagram of a computer included in the magnetic resonance imaging apparatus in the second embodiment is shown. The same elements are shown by the same signs, and their explanations are omitted.

Figure 14:
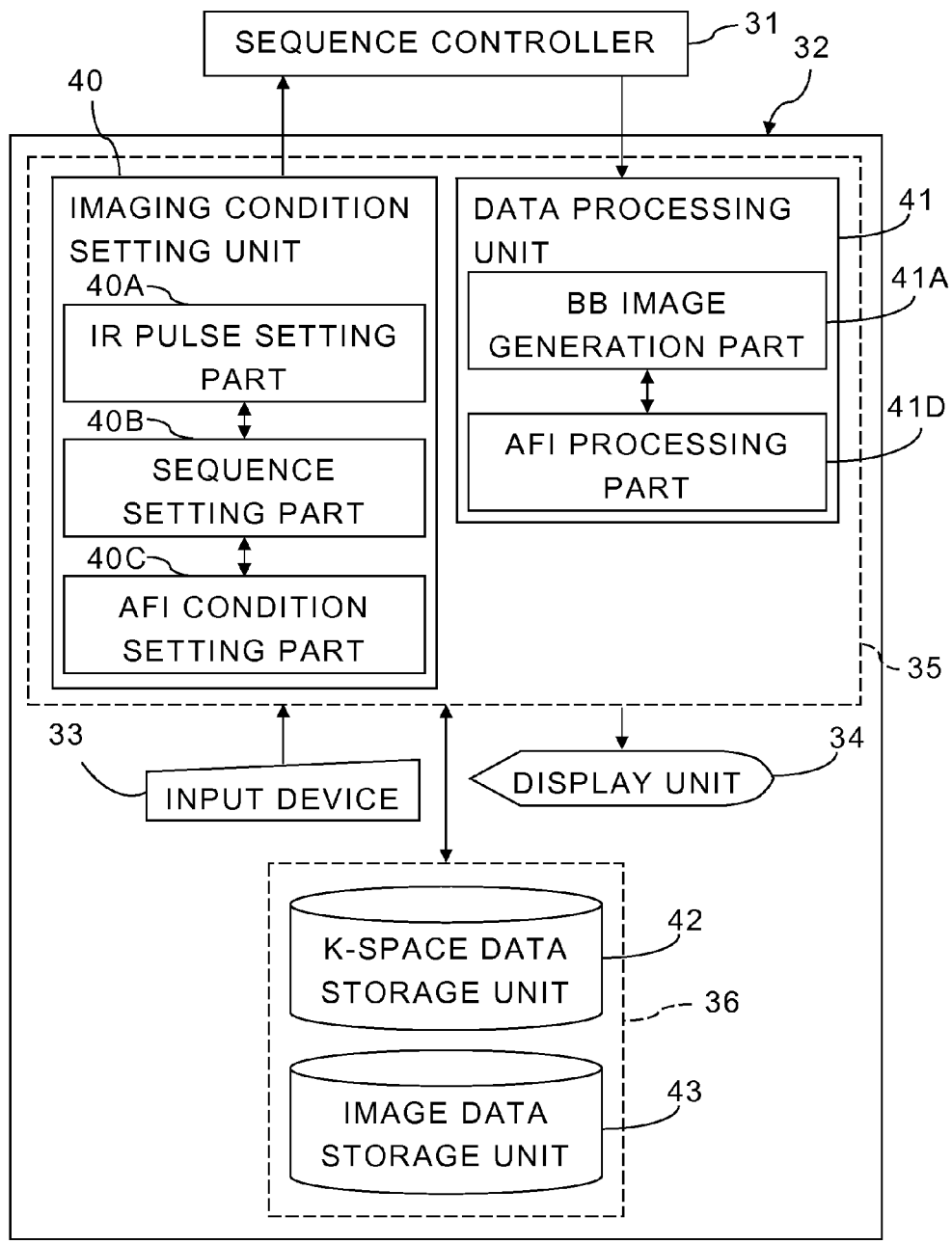
FIG. 14 is a functional block diagram of a computer included in a magnetic resonance imaging apparatus according to the second embodiment of the present invention.

FIG. 14 is a functional block diagram of a computer included in a magnetic resonance imaging apparatus according to the second embodiment of the present invention.

The imaging condition setting unit 40 of the magnetic resonance imaging apparatus in the second embodiment has an AFI condition setting part 40C in addition to the IR pulse setting part 40A and the sequence setting part 40B. On the other hand, the data processing unit 41 has an AFI processing part 41D in addition to the BB image generation part 41A. Note that, the data processing unit 41 may have the WB image generation part 41B and the quantitative image generation part 41C like the first embodiment.

The IR pulse setting part 40A of the imaging condition setting unit 40 has a function to set application conditions including a TI and an application region, of at least one IR pulse as shown in FIG. 3 (A) so that MR signals, of which signal components from tissues show positive values and signal components from blood show negative values, are acquired.

Moreover, the AFI condition setting part 40C has a function to set data acquisition conditions by an AFI method. More specifically, the AFI condition setting part 40C can set conditions such as an asymmetric sampling region of MR signals in a k-space. The asymmetric direction may be set in at least one direction.

The sequence setting part 40B has a function to set a readout sequence of MR signals. Examples of a pulse sequence for acquiring MR signals by an AFI method include an SE series pulse sequence and a GRE series pulse sequence. However, it is preferable to set a two dimensional (2D) FSE sequence or a 3D FSE sequence as a readout sequence of MR signals from a viewpoint of appropriately acquiring phase correction data needed for generating BB image data. The reasons are mentioned later.

Moreover, it is preferable to set a pulse sequence by a VFA (variable flip angle) method for acquiring MR signals with application of multiple refocusing pulses having at least two different flip angles (FAs). When FAs of refocusing pulses are swept by a VFA method, intensities of MR signals in an encode direction of a k-space can be made constant generally.

Therefore, the imaging condition setting unit 40 can set data acquisition conditions for acquiring MR signals, which include signals from tissues having positive values and signals from blood having negative values, from an imaging area of an object P, as MR signals corresponding to a sampling region asymmetric in at least one direction in a k-space, by applying at least one IR pulse under application conditions according to the relaxation times of the blood and the tissues.

On the other hand, the AFI processing part 41D of the data processing unit 41 has a function to generate image data, having a spatial resolution equivalent to that obtained in the case of acquiring all the MR signals in a k-space, by AFI processing based on MR signals corresponding to an asymmetric sampling region in the k-space. Moreover, the BB image generation part 41A has a function to generate BB image data, of which image signals corresponding to blood have negative values, by real part extraction processing for imaging using the real parts of real space signals composing image data generated by AFI processing.

Note that, the phase correction, of real space signals corresponding to background tissues, for generating BB image data is performed as a part of the AFI processing. Moreover, the phase correction of real space signals in the AFI processing is usually performed using self data, i.e., a phase distribution obtained based on MR signals, corresponding to an asymmetric sampling region, acquired by an imaging scan.

Therefore, the second embodiment does not require generation of WB image data and acquisition of MR signals for generating WB image data necessarily. However, when image data, such as WB image data, which can be used as reference image data for the phase correction are generated, a phase correction of real space signals for BB image data may be performed using a phase distribution of the real space signals which compose the reference image data, similarly to the first embodiment.

That is, a phase distribution of reference image data generated using MR signals, different from MR signals acquired for BB image data under data acquisition conditions by the AFI method, as original data can be calculated as phase data for the phase correction. Thereby, the phase correction of the real space signals for BB image data in the AFI processing can be performed using the phase data obtained based on the reference image data.

In this case, it is important that a position gap does not exist between the reference image data for estimating a phase distribution and BB image data which are the target of the phase correction. Moreover, it is important for the reference image data to be generated based on MR signals acquired at timing when the longitudinal magnetizations Mz of tissues and blood show positive values.

Therefore, real space signals for WB image data acquired under the conditions shown in FIG. 3 (B) and FIG. 4 (B) can be used as the reference image data for estimating a phase distribution, as explained in the first embodiment. In this case, the calculation shown by the formula (3) can perform the phase correction.

Moreover, in the case of generating WB image data, WB image data in which background tissues have been suppressed can be generated by subtraction processing which subtracts the BB image data from the WB image data, similarly to the first embodiment.

On the other hand, in the case that the reference image data, such as WB image data, for estimating a phase distribution are not acquired, the phase correction is performed using the self data, i.e., phase data calculated based on MR signals acquired for BB image data. Hereinafter, AFI processing which calculates phase data for the phase correction based on the self data will be described.

The AFI processing for generating BB image data includes filter processing of k-space data by a homodyne filter and phase correction processing of real space data generated by an FT of the k-space data. The homodyne filter is a filter that performs processing equivalent to processing for filling a part, in which data do not exist in a k-space, with complex conjugate data. Therefore, the homodyne filter is a window function whose weight for the asymmetric sampling part of k-space data is different from that for the symmetric sampling part. Then, filling processing of k-space data using the complex conjugate symmetric property is performed by windowing of the k-space data, corresponding to the asymmetric sampling region, with the homodyne filter.

The AFI processing which performs the phase correction of real space data after the filter processing of k-space data is called a Margosian method. On the other hand, the AFI processing which performs the filter processing of k-space data after the phase correction of real space data is called an FIR (finite impulse response) method. The FIR method requires an inverse Fourier transform (IFT) for transforming real space data after the phase correction into k-space data.

Moreover, errors arise in the phase correction because of the homodyne filter processing of k-space data. Accordingly, loop processing for reducing the errors in the phase correction may be performed as a part of the AFI processing, as required. This loop processing is processing which repeats real part extraction processing, composition processing, and phase correction processing. The real part extraction processing is processing which holds only the real parts of real space data after the phase correction and has the imaginary parts of the real space data be zero. The composition processing is processing which combines the sampling part of the original data with the non-sampling part of k-space data obtained by the IFT of the real space data, whose phase has been restored, after the real part extraction processing. The phase correction processing is performed for the real space data obtained by the FT of the k-space data after the composition processing. By such loop processing, changes in imaginary parts of real space data converge down to not more than a threshold. Note that, the technique for reducing the errors in the phase correction, due to the homodyne filter processing, by the loop processing is called a POCS (projection on to convex sets) method.

The phase correction processing in the AFI method is processing to correct phase shifts due to nonuniformity of the static magnetic field. This phase correction processing can be performed using a phase distribution calculated based on MR signals, corresponding to the asymmetric sampling region, acquired by an imaging scan, as mentioned above.

In the conventional AFI processing under the Margosian method or the FIR method, a phase distribution is estimated based on symmetrically sampled k-space data, in a low frequency region near the center of the k-space, out of asymmetrically sampled k-space data. Then, the phase correction of the real space data corresponding to the asymmetric k-space data is performed using the estimated phase distribution.

However, MR signals acquired under data acquisition conditions for real part imaging, as shown in FIG. 3 (A), are in the state that the longitudinal magnetization Mz of blood has inverted by application of an IR pulse. For this reason, the phase of the signal component from the blood has inverted by 180 degrees to the phase of the signal component from the background tissues. Therefore, when the phase correction is performed directly using a phase distribution estimated based on symmetrically sampled k-space data in a low frequency region of the k-space, phase correction errors arise.

Accordingly, the phase data for the phase correction can be calculated based on MR signals in a narrow region in the lower frequency side in at least one direction than the symmetric low frequency region out of the asymmetric sampling region in the k-space. Alternatively, the phase data for the phase correction can be calculated based on MR signals in the symmetric low frequency region out of the asymmetric sampling region, with an appropriate correction. That is, the phase data for the phase correction, obtained based on MR signals in the symmetric low frequency region out of the asymmetric sampling region, can be corrected.

Firstly, an explanation will be made for a method in which the phase data for the phase correction are calculated based on MR signals in a region in the lower frequency side than the symmetric low frequency region out of a sampling region of MR signals and BB image data is generated by the AFI processing, including the phase correction using the obtained phase data, and the extraction processing of the real part signals.

Figure 15:
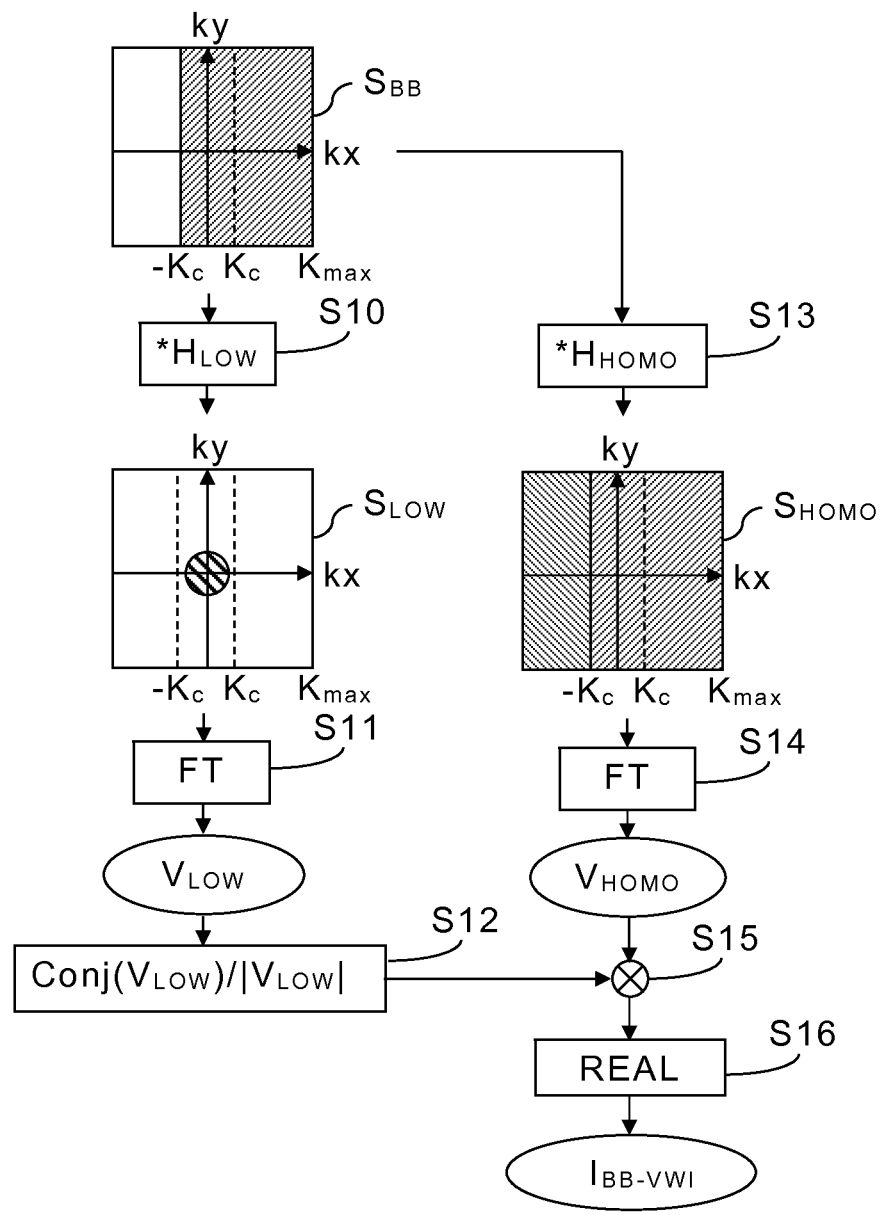
FIG. 15 is a chart showing an example of flow of processing in case of generating an image, using real part signals, by AFI processing based on MR signals in an asymmetric sampling region in the k-space.

FIG. 15 is a chart showing an example of flow of processing in case of generating an image, using real part signals, by AFI processing based on MR signals in an asymmetric sampling region in the k-space.

The graph of the top part in FIG. 15 shows a state that MR signals acquired by an imaging scan have been arranged in a k-space whose vertical axis is ky and horizontal axis is kx. MR signals $S_{BB}$, of which the signal component from blood shows negative values and the signal component from tissues shows positive values, are filled to an asymmetric sampling region of the k-space, as shown in FIG. 15.

In the illustrated example, a sampling region asymmetric in the kx direction has been set. Therefore, the maximum value of the sampling region in the kx direction is the maximum value $K_{max}$ in the k-space while the minimum value is $-K_c$ in the low frequency region. Moreover, the asymmetric sampling region includes a sampling part, whose frequency is from $-K_c$ to $K_c$, symmetric in the kx direction. Surely, a 2D or 3D asymmetric sampling region in the ky direction and/or in the kz direction may be set.

Then, in Step S10, the MR signals $S_{BB}$ corresponding to the asymmetric sampling region are subjected to a LPF (low pass filter) $H_{LOW}$ that has an appropriate intensity. Thereby, k-space data SLOW, in a region in the lower frequency side than the symmetric sampling part ($-K_c \leq kx \leq K_c$) in the low frequency side, are extracted. In the illustrated example, a 2D low frequency region has been extracted with regard to two directions of the kx direction and the ky direction.

Figure 16:
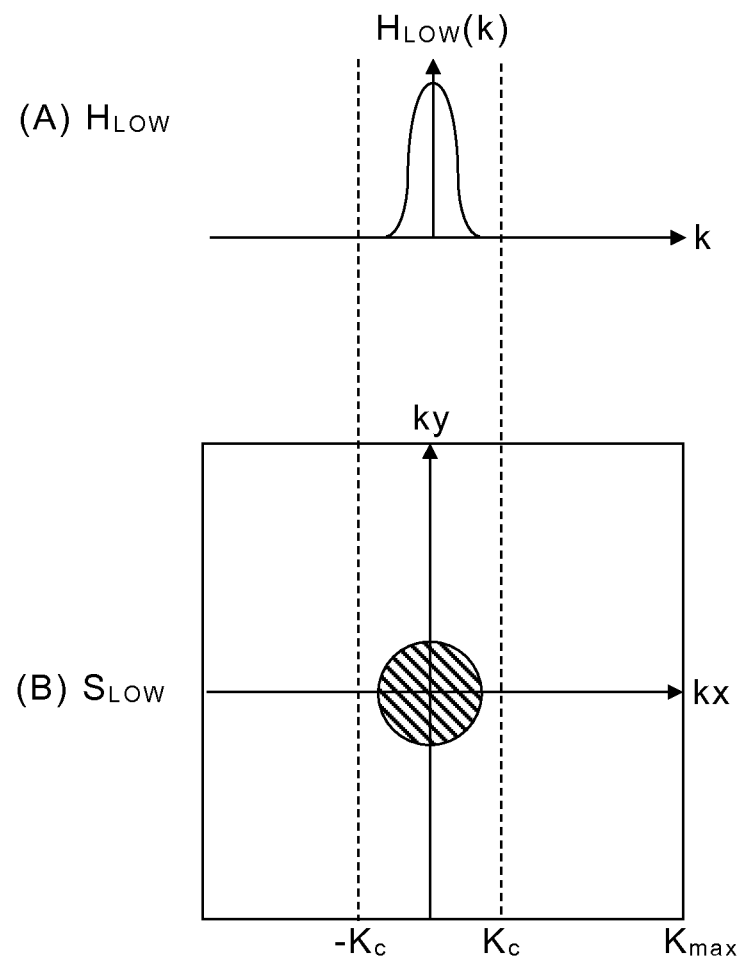
FIG. 16 is graphs showing a characteristic of the LPF shown in Step S10 of FIG. 15.

FIG. 16 is graphs showing a characteristic of the LPF shown in Step S10 of FIG. 15.

In FIG. 16, (A) shows relative intensities $H_{LOW}(k)$ of the LPF in the k direction while (B) shows a low frequency region of the k-space to be extracted by the LPF. In order to extract the k-space data SLOW in the low frequency region as shown in FIG. 16 (B), the LPF $H_{LOW}(k)$ which has an intensity characteristic as shown in FIG. 16 (A) can be used.

When a frequency range to be extracted is determined appropriately, MR signals from blood can be removed while MR signals, in a low frequency region, corresponding to large structural objects that compose the background tissues can be extracted. On the contrary, the intensities $H_{LOW}(k)$ of the LPF can be experientially determined so that the MR signals from the blood can be removed.

Then, the k-space data SLOW, in the low frequency region, extracted by the LPF $H_{LOW}(k)$, can be considered as MR signals, corresponding to the background tissues, whose phases have been shifted by only influence of nonuniformity of the static magnetic field. In other words, the k-space data SLOW, in the low frequency region, which can be considered as the MR signals from the background tissues can be extracted by the LPF $H_{LOW}(k)$.

Therefore, a phase distribution calculated using the k-space data SLOW in the low frequency region after the LPF processing can be used as data for the phase correction for generating BB image data. The phase distribution for the phase correction can be obtained by the transformation of the k-space data SLOW in the low frequency region into real space data $V_{LOW}$ in the low frequency region by an FT, as shown in Step S11, and the calculation shown in Step S12.

On the other hand, in order to obtain image data to be a target of the phase correction, the MR signals $S_{BB}$ corresponding to the asymmetric sampling region are subjected to a homodyne filter $H_{HOMO}$, as shown in Step S13. Thereby, k-space data $S_{HOMO}$ in which data have been filled in the non-sampling region are generated. Then, the real space data $V_{HOMO}$ obtained by the FT of the k-space data $S_{HOMO}$ after the homodyne filter processing are set to be the target of the phase correction, as shown in Step S14.

The phase correction can be performed by the calculation, as shown in Step S15, that the real space data $V_{HOMO}$ after the homodyne filter processing is multiplied by the phase distribution, of the k-space data in the low frequency region, obtained in Step S12.

Next, as shown in Step S16, the real part extraction processing, which outputs the real parts of the real space signals after the phase correction as signal values, is performed. Thereby, BB image data $I_{BB\text{-}VWI}$, which can be provided to a diagnosis as VWI data, can be generated. This BB image data $I_{BB\text{-}VWI}$ become image data of which image signals from the blood show negative values because of imaging of the real parts of the image signals. In addition, the BB image data $I_{BB\text{-}VWI}$ have a spatial resolution, equivalent to that of image data generated by image reconstruction processing of MR signals in the full sampling region of a k-space, by the AFI processing.

Note that, FIG. 15 shows an example case of the AFI processing under the Margosian method that performs the phase correction after the homodyne filter processing. However, the AFI processing may be performed by the FIR method for performing the homodyne filter processing after the phase correction. Moreover, the loop processing by the POCS method may be performed.

Next, a specific example of method for obtaining the phase data for the phase correction based on MR signals in the symmetric low frequency region among the asymmetric sampling region will be described.

Figure 17:
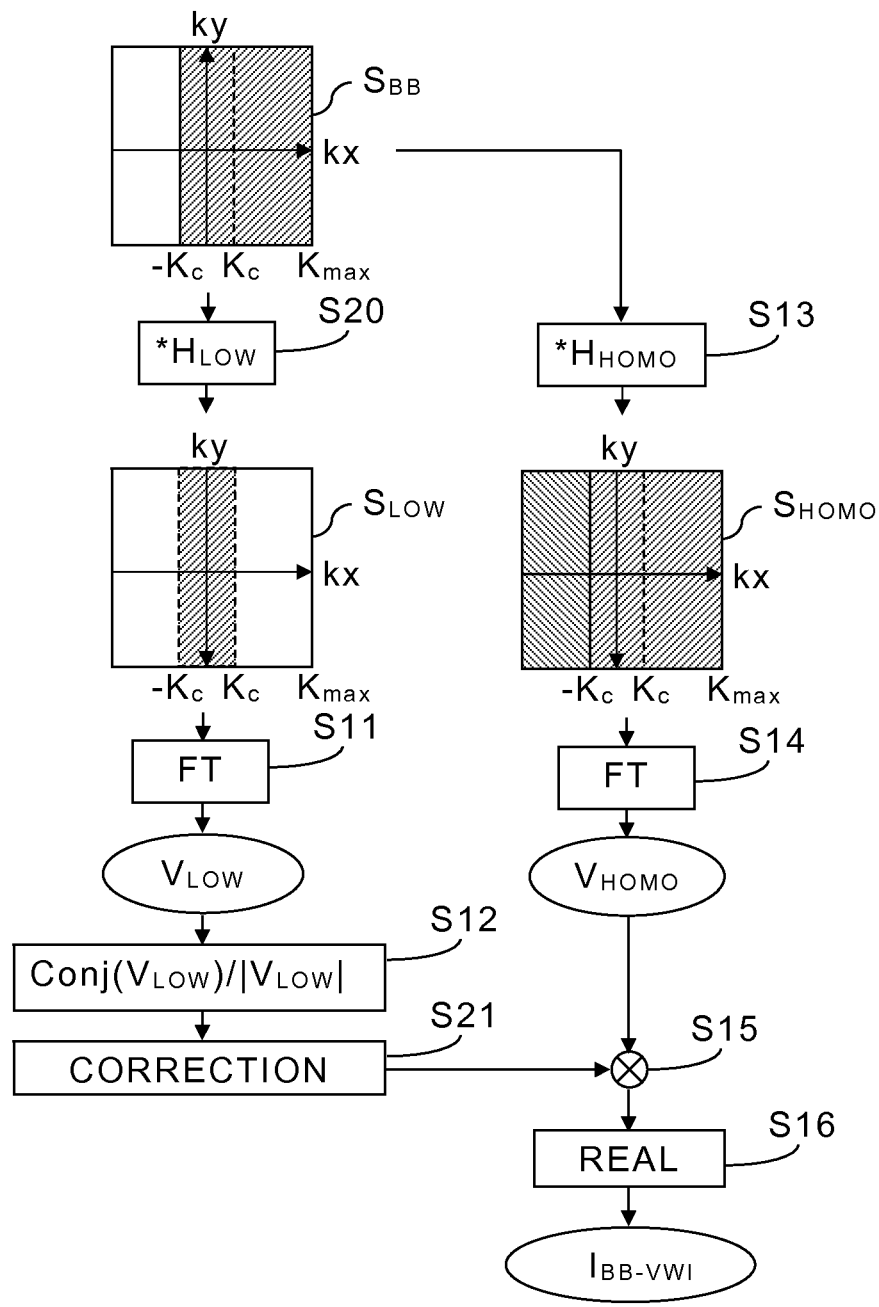
FIG. 17 is a chart showing an example flow of processing in case of imaging real part signals by AFI processing based on MR signals in a symmetric low frequency region out of an asymmetric sampling region in the k-space.

FIG. 17 is a chart showing an example flow of processing in case of imaging real part signals by AFI processing based on MR signals in a symmetric low frequency region out of an asymmetric sampling region in the k-space. In FIG. 17, the same sign is given to each step same as that in FIG. 15, and explanation thereof is omitted.

In the case of calculating the phase data for the phase correction based on MR signals in the symmetric low frequency region ($-K_c \leq kx \leq K_c$), the LPF $H_{LOW}(k)$ for extracting the symmetric low frequency region ($-K_c \leq kx \leq K_c$) is used in the LPF processing of Step S20. Then, a phase distribution of the real space data $V_{LOW}$ obtained by the FT of the k-space data SLOW after the LPF processing is calculated.

However, phases of voxels corresponding to blood have inverted to those corresponding to tissues, in the phase distribution calculated in Step S12. Accordingly, correction processing of the phase distribution is performed so that the phases of the voxels corresponding to the blood become the phases corresponding to the tissues, in Step S21. Subsequently, the phase correction in Step S15 is performed using the phase distribution after the correction. Note that, the AFI processing by the FIR method, corresponding to the example shown in FIG. 17, may be performed.

The correction of the phase distribution of the real space data $V_{LOW}$ can be performed by the following method, for example.

Figure 18:
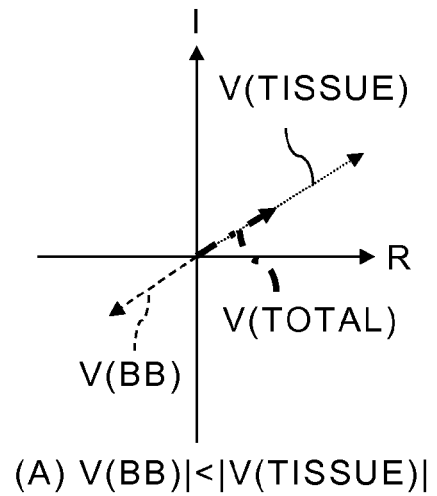
FIG. 18 shows complex planes each expressing an image signal V, before the real part extraction processing and the phase correction, in a voxel in which both blood and a tissue exist.
Figure 18:
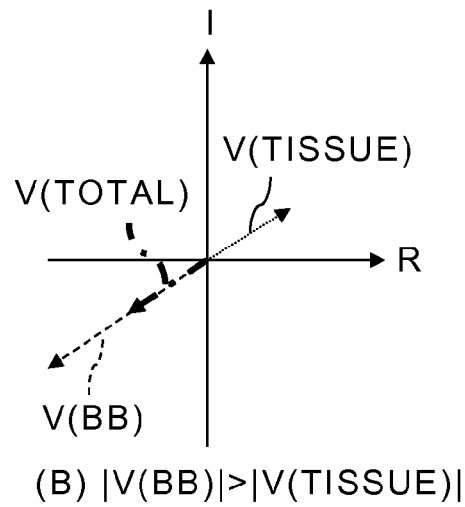

FIG. 18 shows complex planes each expressing an image signal V, before the real part extraction processing and the phase correction, in a voxel in which both blood and a tissue exist.

In (A) and (B) of FIG. 18, each vertical axis represents the imaginary part I of a complex signal while each horizontal axis represents the real part R of the complex signal. Moreover, in (A) and (B) of FIG. 18, each arrow drawn with the dashed-dotted line indicates a vector V(TOTAL) showing a real space signal corresponding to a voxel in which both blood and a tissue exist, each arrow drawn with the solid line indicates a vector V(TISSUE) showing the signal component corresponding to the tissue, and each arrow drawn with the dotted line indicates a vector V(BB) showing the signal component corresponding to the blood.

When MR signals are acquired under IR pulse application conditions so that the longitudinal magnetization Mz(TISSUE) of tissues becomes positive and the longitudinal magnetization Mz(BB) of blood becomes negative, as shown in FIG. 3 (A), and subsequently, the acquired MR signals are converted into real space signals by an FT, the real space signal vector V(TOTAL) at each voxel in which both the blood and the tissue exist becomes a resultant vector of a signal component vector V(TISSUE) corresponding to the tissue and a signal component vector V(BB) corresponding to the blood. Moreover, a phase difference between the signal component vector V(TISSUE) corresponding to the tissue and the signal component vector V(BB) corresponding to the blood is ±π.

Therefore, a phase difference between the real space signal vector V(TOTAL) corresponding to each voxel whose ratio of the blood is less than 50% and the signal component V(TISSUE) corresponding to the background tissues is zero, as shown in FIG. 18 (A). On the contrary, a phase difference between the real space signal vector V(TOTAL) corresponding to each voxel whose ratio of the blood is more than 50% and the signal component V(TISSUE) corresponding to the background tissues is ±π, as shown in FIG. 18 (B).

That is, the relation, shown by the formula (7), according to a component ratio of the real part and the imaginary part composing an amplitude of a real space signal is established at each voxel in which both blood and a tissue exist.

$$arg\{V(TOTAL)\}=arg\{V(TISSUE)\}:|V(BB)|<|V(TISSUE)|=arg\{V(TISSUE)\}\pm\pi:|V(TISSUE)|<|V(BB)| \quad (7)$$

As shown by the formula (7), a difference between a phase of each real space signal corresponding to blood and a phase of each real space signal corresponding to a tissue is |π|. Therefore, voxels corresponding to blood in a phase map showing a phase distribution of real space signals can be detected by determining whether each phase difference, from a phase of a real space signal in a voxel whose ratio of the tissues is 100%, is ±π or not for all the voxels. Then, the phase distribution can be corrected by processing which inverts the phases of the real space signals, in the voxels corresponding to the blood, by 180 degrees. That is, a phase map which can be considered as a phase distribution of real space signals corresponding to the tissues can be produced for the phase correction.

On the other hand, when blood and a tissue are included in a voxel, the partial volume effect, by which an average value of a blood signal value and a tissue signal value becomes a signal value of the voxel, arises. Thereby, pixel values in amplitude image data of real space signals are considered to change smoothly at each boundary between the tissue and the blood, due to the partial volume effect.

That is, a phase map of real space signals shows phase differences of ±π on each boundary of the tissue and the blood while an amplitude map of the real space signals changes smoothly on each boundary of the tissue and the blood.

In consideration of such characters, a concrete algorithm for generating a phase map for the phase correction, by inverting phases of voxels corresponding to blood, can be determined as follows.

Firstly, amplitude image data of the real space data $V_{LOW}$ for estimating a phase distribution are generated, and subsequently, mask image data, in which low signal parts are removed, are generated by performing threshold processing of the amplitude image data, as the first processing. As a result, the mask image data become image data, whose original data are the k-space data SLOW in the symmetric low frequency region ($-K_c \leq kx \leq K_c$) and only voxels corresponding to the tissues or the blood have values, such as 1, which are not zero.

On the other hand, a phase map $\Theta_{orig}$ of the real space data Wow is calculated as the second processing. Next, as the third processing, voxels corresponding to the blood are searched, among voxels in which the mask image data have values, on the phase map $\Theta_{orig}$ and subsequently, phases of the voxels corresponding to the blood are inverted. Thereby, a phase map $\theta_{issue}$ after the correction, which can be considered as a phase distribution of real space data corresponding to the tissues, can be generated.

The search of the voxels corresponding to the blood and the inversion processing of the phases of the voxels corresponding to the blood can be performed by the following processing of all the voxels in which the mask image data have values.

Firstly, a voxel corresponding to a tissue, on the phase map $\Theta_{orig}$ to be a correction target, is set to be a starting point. Then, when a difference between a phase of a focused voxel and a phase of an adjacent voxel is π±α, the phase of the adjacent voxel is shifted by −π. Moreover, when a difference between a phase of a focused voxel and a phase of an adjacent voxel is −π±α, the phase of the adjacent voxel is shifted by +π. Note that, α is a margin determined in consideration of noises.

Figure 19:
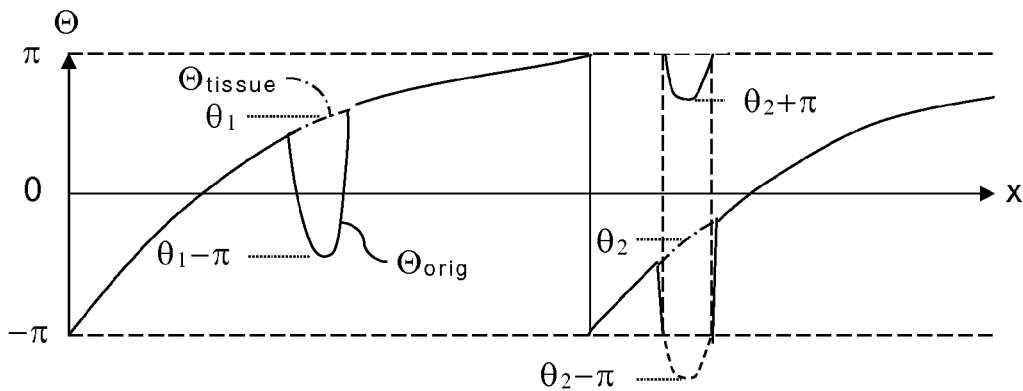
FIG. 19 is a graph showing a phase map of real space signals before and after the correction.

By changing a focused voxel sequentially and shifting the phases of the corresponding voxels by the above-mentioned processing, a phase map $\Theta_{tissue}$, in which the phases of the voxels corresponding to the blood have inverted and which can be considered as a phase distribution of real space signals corresponding to the tissues, can be generated FIG. 19 is a graph showing a phase map of real space signals before and after the correction.

In FIG. 19, the horizontal axis represents positions x of real space signals and the vertical axis represents phases Θ of real space signals. Moreover, the solid lines in FIG. 19 show a phase map $\Theta_{orig}$ of real space signals before the correction, and the dashed-dotted lines show a phase map $\Theta_{tissue}$ of real space signals after the correction.

As shown in FIG. 19, the phase map $\Theta_{orig}$, of the real space signals, in which phases of voxels corresponding to the blood have shifted from phases of voxels corresponding to the tissues by ±π can be corrected into the phase map $\Theta_{tissue}$, without phase differences, which can be considered as a phase distribution corresponding to the tissues.

Note that, in the case that a phase difference more than 2π exists in the phase map $\Theta_{orig}$ before the correction, a folding back arises as illustrated. In this case, a phase $\theta_1−π$ of the blood without a folding back is corrected into a phase $\theta_1$ because the phase inverts by +π. Meanwhile, a phase $\theta_2+π$ of the blood with a folding back inverts by −π and is corrected into the phase $\theta_2$.

Therefore, even when a correction of folding back in a phase distribution is not performed, phases of real space signals, for BB image data, as the target of the phase correction can be corrected appropriately. Note that, the correction of folding back can be performed by shifting a phase of an adjacent voxel, whose phase difference is 2π±α, by −2π and a phase of an adjacent voxel, whose phase difference is −2π±α, by +2π. That is, the phase correction of the real space signals $V_{HOMO}$ shown by the formula (8) using the phase map $\Theta_{tissue}$ tissue after the correction can obtain real space signals $V_{cor}$, after the phase correction, in which the phase shift due to nonuniformity of the magnetic field and folding backs in phase have been corrected.

$$V_{cor} = V_{HOMO} * \exp(-j\Theta_{tissue}) \quad (8)$$

As mentioned above, phase data for the phase correction can be obtained by performing inversion processing, for each voxel, of a phase of a real space signal determined to have shifted by 180 degrees from a phase of a real space signal, corresponding to the tissues, calculated based on MR signals acquired by an imaging scan.

The phase data for the phase correction may be calculated by another method as long as the phase data are generated as a continuous distribution as shown by the dashed-dotted lines of FIG. 19. For example, phase data for the phase correction can be calculated by an interpolation based on a phase distribution of real space signals corresponding to the tissues. The concrete algorithm for calculating a phase distribution for the phase correction by an interpolation can be determined as follows.

At first, as the first processing, amplitude image data of real space data for estimating a phase distribution are generated, and regions corresponding to parts, such as blood and air, other than tissues, are excluded by threshold processing of the amplitude image data. Subsequently, mask image data whose value of each extracted region considered as the tissues is one and value of each excluded region, such as the blood is zero are generated by binarization processing.

Next, as the second processing, a phase map before the correction is generated based on the real space data for estimating the phase distribution, and the generated phase map before the correction is masked by the mask image data. That is, the phase map before the correction is multiplied by the mask image data. As a result, a fragmentary phase map consisting of only phase distributions corresponding to the tissues can be obtained.

Next, as the third processing, parts without phase data are interpolated by an interpolation. Thereby, the phase map, for the phase correction, which can be considered as a phase distribution of the background tissues, can be created.

Furthermore, there is another method of generating phase data by interpolation, which uses a phase distribution of the real space data $V_{HOMO}$ after the homodyne filter processing. The phase map of the real space data $V_{HOMO}$ after the homodyne filter processing has corrected phases of the tissues. Therefore, it can be considered that a phase folding does not exist in the tissues. On the other hand, phases corresponding to the blood have inverted to the phases corresponding to the tissues.

Accordingly, threshold processing of the phase map of the real space data $V_{HOMO}$ after the homodyne filter processing can exclude the phase distributions corresponding to the blood. For this reason, a phase map corresponding to the tissues can be created for the phase correction by an interpolation of the phase map after the threshold processing. In this case, it is expected that phases corresponding to the blood can be detected and corrected with a high accuracy since the target of the threshold processing is not the amplitude image data but the phase map.

In the case where the phase data for the phase correction are generated by a correction of phases corresponding to the blood, as the example in which the phase data for the phase correction are obtained using the phase map of the real space data $V_{HOMO}$ after the homodyne filter processing, not only MR signals in the symmetric sampling part but all the MR signals in the asymmetric sampling region may also be used.

Note that, an improved method of the FIR method, which estimates a phase distribution for the phase correction based on all the k-space data including the part sampled asymmetrically, is called a Modified FIR (MoFIR) method. Therefore, when the phase map for the phase correction is generated with a correction of phases corresponding to the blood, it is also possible to generate BB image data by the AFI processing under the MoFIR method.

Moreover, when MR signals are acquired by an SE series sequence such as an FSE sequence, shift amounts in phases of the background tissues become smaller compared with the case that MR signals are acquired by a GRE series sequence in which a long TE has been set. Therefore, as mentioned above, it is preferable to acquire MR signals by a sequence of the SE series from a viewpoint of obtaining appropriate phase data for the phase correction. Moreover, when MR signals are acquired by the VFA method so that their intensities in an encoding direction become similar, the correction of the phase data for the phase correction can be performed satisfactorily.

Next, the AFI processing to obtain the phase data for the phase correction based on reference image data other than the self data will be described. As mentioned above, in the case of generating image data which can be used as reference image data for the phase correction, the phase correction of real space signals for BB image data can be performed using a phase distribution of real space signals composing the reference image data.

Figure 20:
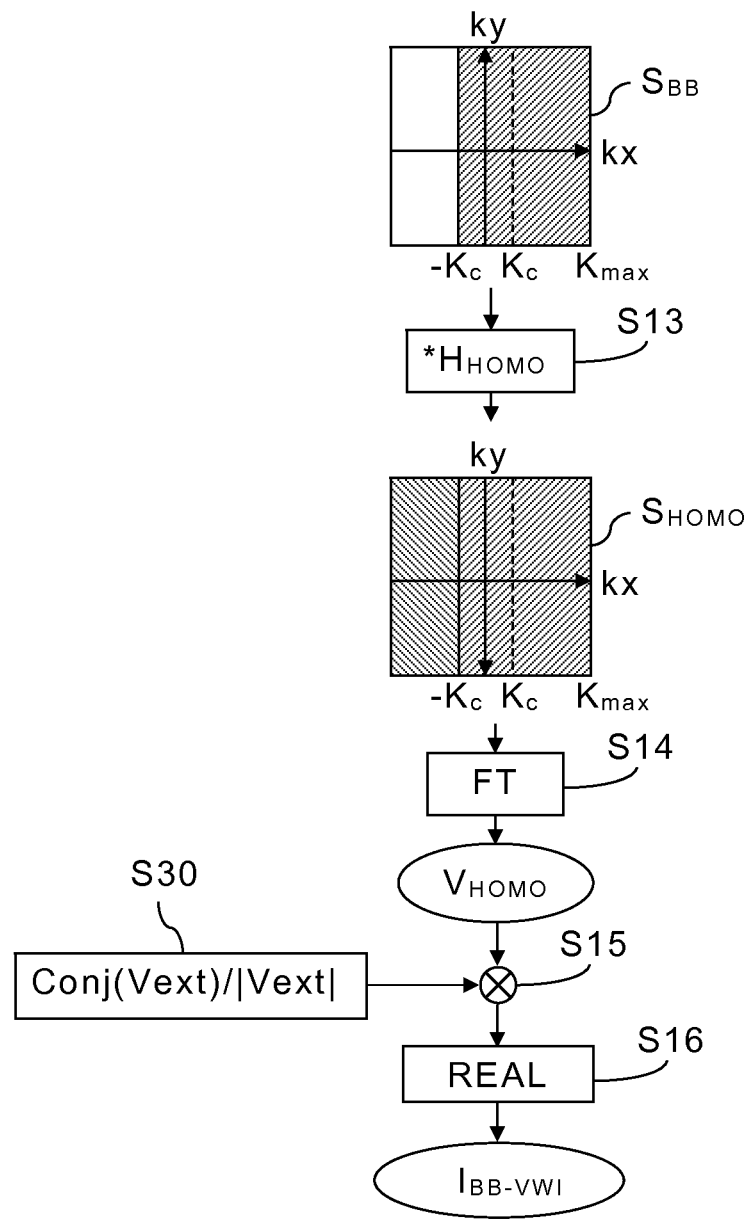
FIG. 20 is a chart showing an example flow of processing in case of performing the phase correction in AFI processing, using phase data obtained based on reference image data.

FIG. 20 is a chart showing an example flow of processing in case of performing the phase correction in AFI processing, using phase data obtained based on reference image data. In FIG. 20, the same sign is given to each step same as that in FIG. 15, and explanation thereof is omitted.

When there are WB image data obtained by the TOF method or the like, or phase distribution information previously obtained for shimming, in addition to WB image data illustrated as an example in the first embodiment, they can be used for reference image data for the phase correction in the AFI processing. In that case, phase data for the phase correction are calculated based on reference data acquired aside from the MR signals $S_{BB}$, which are the self data, corresponding to the asymmetric sampling region, in Step S30.

Specifically, when real space data, consisting of complex image signals, separately obtained as the reference data are represented by Vext, a phase distribution $\exp\{j(x, y)\}$ for the phase correction can be calculated by the formula (9).

$$\exp\{j(x,y)\}=\mathrm{Conj}\{V\mathrm{ext}(x,y)\}/|V\mathrm{ext}(x,y)| \quad (9)$$

Note that, when phases of voxels corresponding to the blood have not inverted in the reference data, the phase data can be calculated using MR signals in an arbitrary frequency region including not only the low frequency region but also the frequency range corresponding to the background tissues. For example, the phase data for the phase correction can also be calculated using the MR signals in all the sampling region. That is, as long as phases of real space data corresponding to the background tissues can be corrected, the AFI processing, including the homodyne filter processing, whose original data are MR signals corresponding to the asymmetric sampling region can be performed because the conjugate symmetric property is established in a k-space.

Moreover, the AFI processing can also be performed by another method, such as the FIR method or the MoFIR method though FIG. 20 shows an example of the AFI processing under the Margosian method.

The data processing unit 41 having the functions mentioned above functions as a data processing unit for generating BB-VWI image data, in which blood is depicted as a lower signal region than that of tissues, by data processing, which includes a phase correction of real space signals generated based on MR signals in an asymmetric sampling region and processing to perform imaging using the real parts of the real space signals after the phase correction.

That is, the magnetic resonance imaging apparatus in the second embodiment is an apparatus configured to acquire BB image data by the AFI method, the IR method, and the real part imaging.

According to the second embodiment, BB image data, having a spatial resolution equivalent to the spatial resolution obtained in the case of acquiring all the MR signals in a k-space, can be acquired by acquiring MR signals from an asymmetric sampling region in a k-space. Therefore, an imaging period can be shortened. Furthermore, a CNR of BB image data can be improved by the real part imaging and an IR pulse application.

Third Embodiment

In a magnetic resonance imaging apparatus in the third embodiment, a data acquisition method of MR signals differs from that of the magnetic resonance imaging apparatus 20 in the first embodiment. Specifically, the magnetic resonance imaging apparatus in the third embodiment acquires the first MR signals $S_{BB}$ for generating BB image data by applying an IR pulse or IR pulses and the second MR signals $S_{WB}$ for generating WB image data with applying no IR pulse under a TOF method. For this reason, with regard to the third embodiment, only data acquisition conditions and a flow of image generation will be described with reference to drawings, explanation of the same matters as those in the first embodiment is omitted.

Note that, the third embodiment can be considered as a kind of the first embodiment if the acquisition of the second MR signals $S_{WB}$ by the TOF method is interpreted to be an acquisition, in which an intensity of an IR pulse is zero, similar to an acquisition under the conditions shown in FIG. 7 (B). Moreover, as mentioned above, in the case that WB image data is generated in the second embodiment, MR signals for generating the WB image data may also be acquired by the TOF method.

Figure 21:
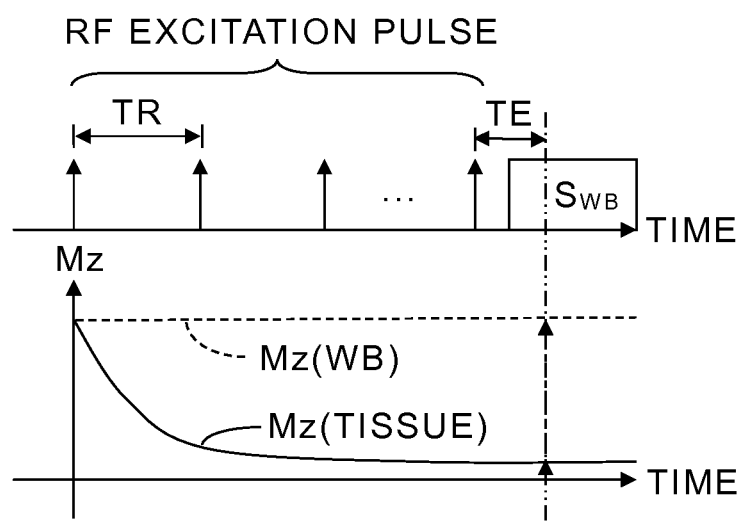
FIG. 21 is a conceptual chart of a TOF sequence set, in order to acquire the second MR signals $S_{WB}$ for WB image data, in the magnetic resonance imaging apparatus according to the third embodiment of the present invention.

FIG. 21 is a conceptual chart of a TOF sequence set, in order to acquire the second MR signals $S_{WB}$ for WB image data, in the magnetic resonance imaging apparatus according to the third embodiment of the present invention.

In FIG. 21, the horizontal axis represents time, and the vertical axis of the graph represents the longitudinal magnetizations Mz of blood and tissues. As shown in FIG. 21, the second MR signals $S_{WB}$ for WB image data can be acquired by the TOF method without applying an IR pulse. The TOF method is a data acquisition method of an MRA, which acquires MR signals, having large intensities, from blood flowing into an imaging area, by a GRE series of sequence or the like, by taking advantage of the inflow effect of the blood.

Specifically, an RF excitation pulse is repeatedly applied to an imaging area with a TR shorter than the longitudinal relaxation time (T1) of the tissues. Therefore, the longitudinal magnetization Mz(TISSUE) of the tissues decreases gradually and asymptotically toward zero. As a result, the intensities of the MR signals from the tissues are suppressed. On the other hand, the longitudinal magnetization Mz(BB) of the blood which flows into the imaging area from the outside does not decrease because the blood which flows into the imaging area is not influenced by the RF excitation pulses. Therefore, the MR signals from the blood that flows into the imaging area have large intensities. Thereby, the second MR signals $S_{WB}$ in which the MR signals from the tissues have suppressed intensities while the MR signals from the blood have positive values can be acquired at a data acquisition timing.

On the other hand, the first MR signals $S_{BB}$, of which the MR signals from the blood show negative values, can be acquired for BB image data by an IR sequence whose TI is adjusted appropriately according to each of the relaxation times of the blood and the tissues.

Note that, ISCE (inclined slab for contrast enhancement) pulses may be used as RF pulses for acquiring at least one of the first MR signals $S_{BB}$ and the second MR signals $S_{WB}$. The ISCE pulses are also called TONE (tilted optimized non-saturated excitation, ramped RF) pulses. The ISCE pulses are RF pulses whose FA sizes are inclined in a slab direction so that an FA size in an exit side of a blood flow becomes larger than an FA size in an entrance side of the blood flow. The ISCE pulses are usually used in order to improve a depiction ability of peripheral vessels in a TOF method. However, ISCE pulses may be used for acquiring both the second MR signals $S_{WB}$ for WB image data by a TOF method and the first MR signals $S_{BB}$ for BB image data by an IR method. More effectively, ISCE pulses may be used only for acquisition of the second MR signals $S_{WB}$ by a TOF method because it can be assumed that phases are not influenced by the transverse magnetizations.

Figure 22:
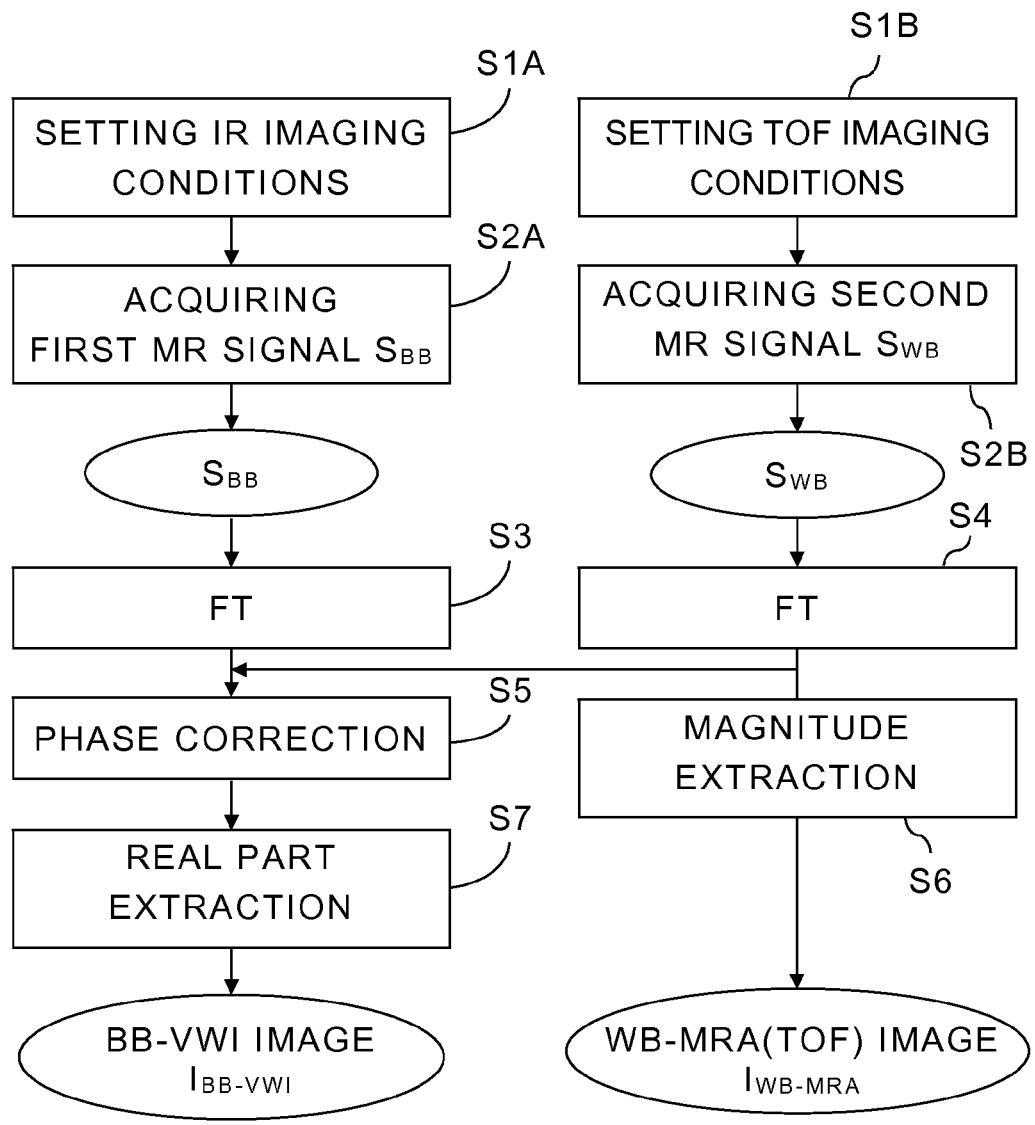
FIG. 22 is a flow chart which shows a flow in case of generating BB image data and WB image data by acquisition of the first MR signals $S_{BB}$ under an IR method and acquisition of the second MR signals $S_{WB}$ under a TOF method.

FIG. 22 is a flow chart which shows a flow in case of generating BB image data and WB image data by acquisition of the first MR signals $S_{BB}$ under an IR method and acquisition of the second MR signals $S_{WB}$ under a TOF method. In the flow chart shown in FIG. 22, the same sign is given to each step same as that in the flow chart shown in FIG. 13, and detailed explanation thereof is omitted.

Firstly, in Step S1A, the imaging condition setting unit 40 sets an IR sequence whose TI has been appropriately set for acquiring the first MR signals $S_{BB}$. Then, in Step S2A, the first MR signals $S_{BB}$ are acquired according to the set IR sequence. Next, in Step S3, the BB image generation part 41A performs the FT of the first MR signals $S_{BB}$. Thereby, the first real space signals $V_{BB}$ are generated.

On the other hand, in Step S1B, the imaging condition setting unit 40 sets a TOF sequence in which conditions including a TR and the number of repetition times have been appropriately set for acquiring the second MR signals $S_{WB}$. Then, in Step S2B, the second MR signals $S_{WB}$ are acquired according to the set TOF sequence. Next, in Step S4, the WB image generation part 41B performs the FT of the second MR signals $S_{WB}$. Thereby, the second real space signals $V_{WB}$ are generated. Next, in Step S6, the WB image generation part 41B performs magnitude extraction processing which calculates absolute values of the second real space signals $V_{WB}$ which are complex signals. Thereby, TOF image data can be generated as WB-MRA image data $I_{WB-MRA}$.

On the other hand, in Step S5, the BB image generation part 41A performs a phase correction of the first real space signals $V_{BB}$, using a phase correction amount obtained based on a phase distribution of the second real space signals $V_{WB}$. Next, in Step S7, the BB image generation part 41A performs the real part extraction processing which calculates real parts of the first real space signals $V_{BB}$ cor after the phase correction. Thereby, BB-VWI image data $I_{BB-VWI}$ can be generated.

Note that, BB-VWI image data $I_{BB-VWI}$ may be generated by an IR sequence after the generation of WB-MRA image data $I_{WB-MRA}$ by a TOF sequence. Moreover, conditions for the TOF method are set to conditions such that at least a phase distribution of the second real space signals $V_{WB}$ can be assumed as a phase distribution of the first real space signals $V_{BB}$ obtained by an IR method. Therefore, the TE of the TOF sequence is set to be same as that of the IR sequence.

According to the magnetic resonance imaging apparatus in the third embodiment as mentioned above, a scan for acquiring data for the phase correction for generating BB-VWI image data $I_{BB-VWI}$ can be omitted. Specifically, data for the phase correction for generating BB-VWI image data $I_{BB-VWI}$ can be obtained using data acquired for generating TOF image data effectively. For this reason, an imaging period can be shortened and a BB image and a WB image can be acquired more efficiently.

Other Embodiments

While certain embodiments have been depicted, these embodiments have been presented by way of example only, and are not intended to limit the scope of the inventions. Indeed, the novel methods and systems depicted herein may be embodied in a variety of other forms; furthermore, various omissions, substitutions and changes in the form of the methods and systems depicted herein may be made without departing from the spirit of the inventions. The accompanying claims and their equivalents are intended to cover such forms or modifications as would fall within the scope and spirit of the inventions.

For example, similar imaging can be performed in a case that a fluid, such as cerebrospinal fluid (CSF) is imaged though a case of imaging blood has been explained in each of the above-mentioned embodiments. Furthermore, MR image data in which a specific component, such as a specific tissue, as well as a fluid, such as blood, has been enhanced as high signal values or suppressed as low signal values can also be generated.

That is, in the first or third embodiment, the first MR signals, which include MR signals from fluid having negative values, and the second MR signals, which include MR signals from the fluid having positive values, can be acquired from a same imaging area of an object P by applying an IR pulse or IR pulses under application conditions according to a relaxation time of the fluid. Then, the first image data, in which the fluid is depicted as lower signal regions than those of tissues, and the second image data, in which the fluid is depicted as higher signal regions than those of the tissues, can be generated based on the first MR signals and the second MR signals. Note that, it is effective from a viewpoint of improving a contrast to acquire the first MR signals so that MR signals from the tissues have positive values, by applying an IR pulse or IR pulses under application conditions according to a relaxation time of the tissues in addition to a relaxation time of the fluid.

On the other hand, in the second embodiment, MR signals, whose signals from the second component to be an enhanced target show positive values and signals from the first component to be a suppression target show negative values, corresponding to a sampling region asymmetric in at least one direction in a k-space can be acquired from an imaging area of an object by applying an IR pulse or IR pulses under application conditions according to relaxation times of the first component and the second component. Then, image data in which the first component is depicted as lower signal regions than those of the second component can be generated by data processing including a phase correction, which uses phase data calculated based on MR signals, of real space signals generated based on the MR signals corresponding to the asymmetric sampling region and imaging processing of real parts of the real space signals after the phase correction.

Therefore, the above mentioned second embodiment corresponds to a case that the first component is blood and the second component is background tissues. In the second embodiment, the first component may be an abnormal tissue while the second component may be normal tissues so that imaging can be performed for distinguishing the abnormal tissue from the normal tissues.

What is claimed is:

1. A magnetic resonance imaging (MRI) apparatus comprising:
   at least one radio frequency (RF) coil disposed within static and gradient magnetic field generators, an RF transmitter and an RF receiver coupled to said at least one RE coil, and at least one control computer connected to control said gradient magnetic field generators, said RF transmitter, said RF transmitter and said RF receiver to execute MRI data acquisition sequences and to process acquired MRI signals; said at least one control computer being configured to
   acquire first and second magnetic resonance signals from a flowing fluid within same imaging area of an object using at least one inversion recovery pulse related to a MR relaxation time of a flowing fluid within the object, the first magnetic resonance signals, from the fluid including negative values, the second magnetic resonance signals from the fluid including positive values, and
   generate first and second image data based, respectively, on the first and second magnetic resonance signals, the first image data depicting the fluid as a lower signal region than a signal region of surrounding tissue, the second image data depicting the fluid as a higher signal region than a signal region of the surrounding tissue;
   the first image data being generated with a phase correction based on the second magnetic resonance signals.

2. The magnetic resonance imaging apparatus of claim 1, wherein:
   phase correction of real space signals is performed using phase data and the first image data is generated by imaging real parts of the real space signals after the phase correction, the real space signals being generated based on the first magnetic resonance signals, the phase data being obtained based on the second magnetic resonance signals.

3. The magnetic resonance imaging apparatus of claim 1, wherein:
   the at least one inversion recovery pulse is applied repeatedly and a part of the first magnetic resonance signals and a part of the second magnetic resonance signals are alternately acquired between repeated applications of the at least one inversion recovery pulse.

4. The magnetic resonance imaging apparatus of claim 1, wherein:
   a first inversion recovery pulse is applied in a first application region and a second inversion recovery pulse is applied in a second application region, the first application region being larger than the imaging area, the second application region being larger than the imaging area and smaller than the first application region, the first application region being set to make magnetic resonance signals from the fluid, having flowed from an outside into the imaging area, show negative values at acquisition timing of the first magnetic resonance signals, the second application region being set to make magnetic resonance signals from the fluid, having flowed from an outside into the imaging area, show positive values at acquisition timing of the second magnetic resonance signals; and
   longitudinal relaxation weighted image data is generated as the first image data and the second image data.

5. The magnetic resonance imaging apparatus of claim 1, wherein:
   a first inversion recovery pulse is applied and a second inversion recovery pulse is applied, the first inversion recovery pulse being applied in each of a first application region and a second application region after a predetermined time interval, the first application region being larger than the imaging area, the first application region being set to make magnetic resonance signals from the fluid, having flowed from an outside into the imaging area, show negative values at acquisition timing of the first magnetic resonance signals, the second application region being larger than the imaging area and smaller than the first application region, the second inversion recovery pulse being applied twice in a third application region with the predetermined time interval or another predetermined time interval, the third application region being larger than the imaging area and smaller than the first application region, the third application region being same as or different from the second application region, the third application region being set to make magnetic resonance signals from the fluid, having flowed from an outside into the imaging area, show positive values at acquisition timing of the second magnetic resonance signals; and
   transverse relaxation weighted image data or proton density weighted image data is generated as the first image data and the second image data.

6. The magnetic resonance imaging apparatus of claim 1, wherein:
   an inversion recovery pulse is applied in an application region outside the imaging area and the second magnetic resonance signals are acquired with no inversion recovery pulse being applied, the application region being set to make magnetic resonance signals from the fluid, having flowed from an outside into the imaging area, show negative values at acquisition timing of the first magnetic resonance signals; and
   transverse relaxation weighted image data or proton density weighted image data is generated as the first image data and the second image data.

7. The magnetic resonance imaging apparatus of claim 1, wherein:
   the first magnetic resonance signals are acquired by applying the at least one inversion recovery pulse and the second magnetic resonance signals are acquired without applying an inversion recovery pulse, the second magnetic resonance signals including magnetic resonance signals from the tissue and magnetic resonance signals from the fluid having flowed into the imaging area, intensities of the magnetic resonance signals from the tissue being suppressed by repeatedly applying a radio frequency excitation pulse to the imaging area with a repetition time shorter than a longitudinal relaxation time of the tissue, the magnetic resonance signals from the fluid having positive values.

8. The magnetic resonance imaging apparatus of claim 1, wherein:
at least multiple sets of the first magnetic resonance signals are acquired, the sets respectively corresponding to at least one of (a) different inversion times and (b) different echo times; and
image data is generated showing at least one of a distribution of a longitudinal relaxation time, a distribution of a transverse relaxation time, a distribution of a permeability of the fluid to the tissue and blood dynamic state image data, based on at least the multiple sets of the first magnetic resonance signals.

9. The magnetic resonance imaging apparatus of claim 1, wherein:
the first magnetic resonance signals and the second magnetic resonance signals are acquired using inversion times which are effectively the same; and
the second image data is generated as image data, in which a depiction of the tissue is suppressed and the fluid is depicted, by subtraction processing between image data generated based on the first magnetic resonance signals and image data generated based on the second magnetic resonance signals.

10. The magnetic resonance imaging apparatus of claim 1, wherein:
the first magnetic resonance signals and the second magnetic resonance signals are acquired after applying a common inversion recovery pulse.

11. The magnetic resonance imaging (MRI) apparatus comprising:
at least one radio frequency (RF) coil disposed within static and gradient magnetic field generators, an RE transmitter and an RF receiver coupled to said at least one RF coil, and at least one control computer connected to control said gradient magnetic field generators, said RF transmitter, said RF transmitter and said RF receiver to execute MRI data acquisition sequences and to process acquired MRI signals; said at least one control computer being configured to
acquire magnetic resonance signals from an imaging area of an object by applying at least one inversion recovery pulse related to relaxation times of a first component to be a suppression target and a second component to be a weighted target, the magnetic resonance signals including signals, having negative values, from the first component and signals, having positive values, from the second component, the magnetic resonance signals corresponding to an asymmetric sampling region in at least one direction in k-space; and
generate real space image data including a phase correction based on the acquired magnetic resonance signals, the image data depicting the first component as a lower signal region than a signal region of the second component.

12. The magnetic resonance imaging apparatus of claim 11, wherein:
the magnetic resonance signals are acquired by a spin echo series of an MRI pulse sequence.

13. The magnetic resonance imaging apparatus of claim 12, wherein:
the magnetic resonance signals are acquired by applying refocus pulses having at least two different flip angles.

14. The magnetic resonance imaging apparatus of claim 11, wherein:
the phase correction is performed using phase data obtained based on the magnetic resonance signals.

15. The magnetic resonance imaging apparatus of claim 14, wherein:
the phase data is obtained based on magnetic resonance signals in a narrow region in a lower frequency side in at least one direction than a symmetric low frequency region out of the sampling region.

16. The magnetic resonance imaging apparatus of claim 14, wherein:
the phase data is obtained based on magnetic resonance signals in a symmetric low frequency region out of the sampling region.

17. The magnetic resonance imaging apparatus of claim 14, wherein:
the phase data is obtained by inverting a phase of a real space signal determined to have shifted by 180 degrees from a phase of a real space signal corresponding to the second component, the real space signal corresponding to the second component being obtained based on the magnetic resonance signals, inversion of the phase being performed for each voxel.

18. The magnetic resonance imaging apparatus of claim 14, wherein:
the phase data is obtained by an interpolation based on a phase distribution of real space signals corresponding to the second component, the real space signals corresponding to the second component being obtained based on the magnetic resonance signals.

19. The magnetic resonance imaging apparatus of claim 11, wherein:
the phase correction is performed using phase data obtained based on reference image data, the reference image data being generated using original data which are magnetic resonance signals different from the magnetic resonance signals acquired from the imaging area.

20. The magnetic resonance imaging apparatus of claim 11, wherein:
magnetic resonance signals having the negative values are acquired from blood as the first component and magnetic resonance signals having the positive values are acquired from a tissue as the second component.

21. A magnetic resonance imaging (MRI) method comprising:
controlling gradient magnetic field generators, a radio frequency (RF) transmitter and an RF receiver coupled to at least one RF coil disposed in an imaging volume of an MRI system to effect:
acquiring first and second magnetic resonance signals from a same imaging area of an object by applying at least one inversion recovery pulse according to a relaxation time of a fluid flowing within the object, the first magnetic resonance signals from the fluid, having negative values, the second magnetic resonance signals from the fluid, having positive values; and
generating first and second image data, respectively based on the first and second magnetic resonance signals, the first image data depicting the fluid as a lower signal region than a signal region of a tissue, the second image data depicting the fluid as a higher signal region than a signal region of the tissue;

wherein the first image data are generated with a phase correction based on the second magnetic resonance signals.

* * * * *